(12) United States Patent
Rhee et al.

(10) Patent No.: US 6,838,555 B2
(45) Date of Patent: Jan. 4, 2005

(54) HANSENULA POLYMORPHA MUTANTS AND PROCESS FOR THE PREPARATION OF RECOMBINANT PROTEINS USING THE SAME

(75) Inventors: Sangki Rhee, Seoul (KR); Euisung Choi, Taejon (KR); Hyunah Kang, Taejon (KR); Junghoon Sohn, Taejon (KR); Junghoon Bae, Taejon (KR); Moowoong Kim, Taejon (KR); Michael Agaphonov, Moscow (RU); Myungkuk Kim, Seoul (KR)

(73) Assignee: Korea Research Institute of Bioscience & Biotechnology, Taejon (KR)

( * ) Notice: Subject to any disclaimer, the term of this patent is extended or adjusted under 35 U.S.C. 154(b) by 93 days.

(21) Appl. No.: 09/993,192

(22) Filed: Nov. 14, 2001

(65) Prior Publication Data

US 2002/0150983 A1 Oct. 17, 2002

Related U.S. Application Data

(62) Division of application No. 09/674,617, filed as application No. PCT/KR00/00173 on Mar. 4, 2000, now abandoned.

(30) Foreign Application Priority Data

Mar. 4, 1999 (KR) .......................................... 1999-7177
Mar. 3, 2000 (KR) ....................................... 2000-10743

(51) Int. Cl.$^7$ ............................................... C07H 21/04
(52) U.S. Cl. .................. 536/23.74; 536/23.1; 536/23.2; 435/4; 435/6; 435/41; 435/69.1; 435/71.1; 435/320.1; 435/255.1; 435/256.1
(58) Field of Search ......................... 435/4, 6, 41, 69.1, 435/71.1, 320.1, 243, 254.1, 255.1, 255.6; 536/23.1, 23.2, 23.74

(56) References Cited

FOREIGN PATENT DOCUMENTS

WO    WO 00/52133    *   8/2000

OTHER PUBLICATIONS

Clare, Jeffrey J. et al., Production of mouse epidermal growth factor in yeast: high–level secretion using Pichia pastoris strains containing multiple gene copies, Elsevier Science Publishers B.V., 1991, pp. 205–212.

Hodgkins, Martin et al., Expression of the Glucose Oxidase Gene from Aspergillus niger in Hansenula polymorpha and its Use as a Reporter Gene to Isolate Regulatory Mutations, Yeast, vol. 9, pp. 625–635, Jan. 14, 1993.

Hinnen, Albert et al., Gene Expression in Recombinant Yeast, pp. 121–193, Ciba–Geigy AG, Basel, Switzerland.

Romanos, Michael A. et al., Recombinant Bordetella pertussis pertactin (P69) from the yeast Pichia pastoris: high–level production and immunological properties, Vaccine, vol. 9, Dec. 1991, pp. 901–906.

* cited by examiner

*Primary Examiner*—James Ketter
*Assistant Examiner*—David A. Lambertson
(74) *Attorney, Agent, or Firm*—Fox Rothschild LLP

(57) ABSTRACT

Disclosed are *Hansenula polymorpha* mutants useful as host cells through which various proteins can be produced as being intact at high yield and a process for preparing recombinant proteins using the host cells. Using various vectors, *Hansenula polymorpha* is made to be a mutant which is deprived of methanol assimilating ability and incapable of utilizing methanol as a carbon source. This *Hansenula polymorpha* mutant is used as a high yield host to produce recombinant proteins without continuous feeding of methanol, with the aid of an expression cassette carrying a promoter capable of inducing the expression at a low concentration of methanol. Further, the mutant is also lacking in carboxypeptidase Y, protease Y and/or carboxypeptidase a activity, so the recombinant protein of interest is not degraded at its carboxyl terminal when being expressed in the cell. Thus, intact recombinant protein can be obtained. Also, there is disclosed a pop-out technique in which a recombinant protein expression cassette is inserted into a MOX gene site of the mutant and is allowed to pop out therefrom, thereby utilizing the mutant as a host for general use in producing various proteins of interest.

1 Claim, 13 Drawing Sheets

FIG. 9

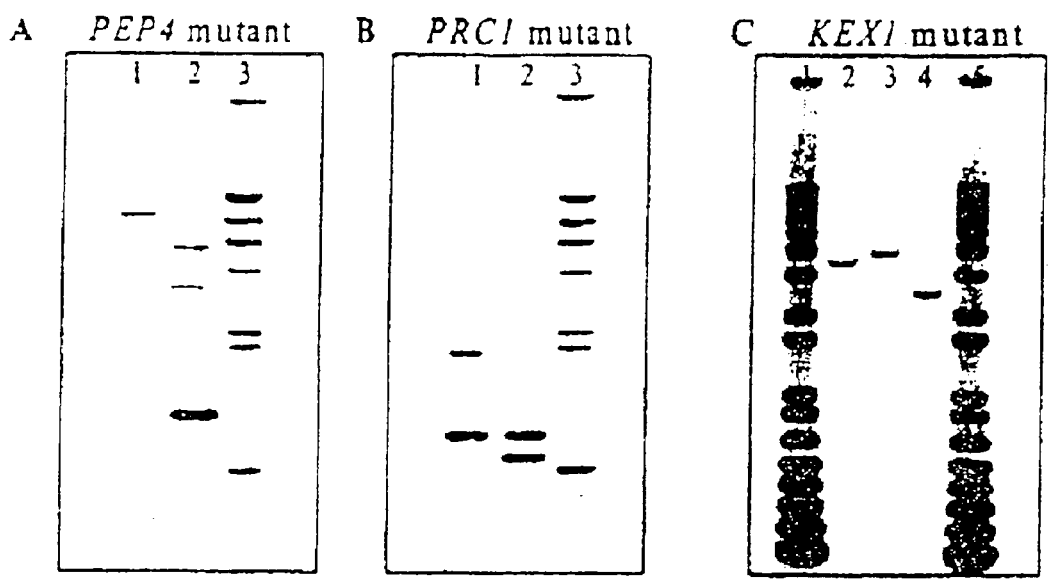

A. Lane 1 : *H. polymorpha* UR2/*EcoR*V
   Lane 2 : *pep4* mutant/*EcoR*V
   Lane 3 : DIG-λ/*Hind*III size marker
   probe  : DIG labeled pHDP4/*SacI*/*Hind*III 2kb fragment B. Lane 1 : *H. polymorpha* UR2/*EcoR*I
   Lane 2 : *prc1* mutant/*EcoR*I
   Lane 3 : DIG-λ/*Hind*III size marker
   probe  : DIG labeled pHDY2/*EcoR*I 1.5kb fragment C. Lane 1.5 : DIG-1 kb size marker
   Lane 2 : *H. polymorpha* DL1/*Xho*I
   Lane 3 : *kex1* mutant/*Xho*I
   Lane 4 : URA3 gene pop-out /*Xho*I
   probe  : DIG labeled pKH4.5/*Xho*I 3.5kb fragment

FIG. 12
A. 2% Glucose + 0.67% YNB + LEU + TRP
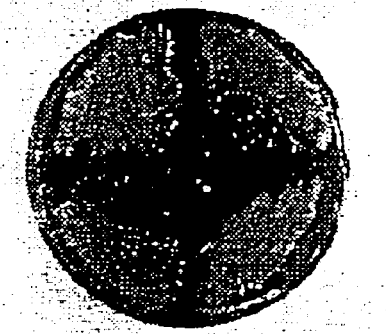
B. 0.5% Methanol + 0.67% YNB + LEU + TRP
C. 2% Glucose + 0.67% YNB + LEU
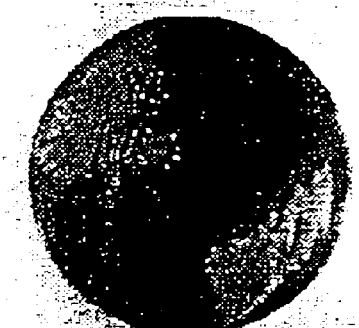
D. 2% Glucose + 0.67% YNB + TRP
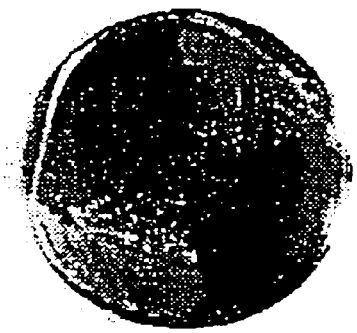
E. 2% Glucose + 2% Peptone + 1% Yeast extarct
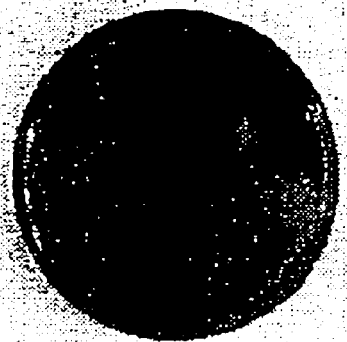
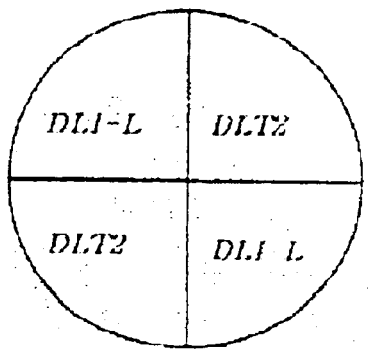

YGF: Your Favorite Gene(YFG)

METHANOL CONCENTRATION (%)

SEQUENCE LISTING

```
<160> NUMBER OF SEQ ID NOS: 9

<210> SEQ ID NO 1
<211> LENGTH: 2218
<212> TYPE: DNA
<213> ORGANISM: Hansenula polymorpha DL1
<300> PUBLICATION INFORMATION:
<308> DATABASE ACCESSION NUMBER: U67174
<309> DATABASE ENTRY DATE: 1996-08-17
<313> RELEVANT RESIDUES: (1)..(2218)

<400> SEQUENCE: 1
ctcgagtatg attactttgt cttaattttt atttggtgta attttttact accattttaa      60
tgacgtggtg tacgggtgtg aatacataaa cacctcagta gccatagcag ctaccatgga     120
tgatagggca cttttggaaa aggaatctga aaacaagaag aagcacggca tacggtggtc     180
aacagctcaa gaaaggccaa tgcgataaat ctcattttta tacgaacacc caccgaagcc     240
cttatcggtc ttttgacgca gcagcttaat tatctgaggc tggttatcaa tttttgcctt     300
ccagataaaa tatattttcc ctatttatat tccatccgtt tatcctaggc aatcgtccaa     360
aaaaacaaga attctgttat atttcaattc ccattatgaa gctctcgatg tctattctgg     420
ccctagtggc cactagcatt gggtcggcgc aagccgctgc catcaaaaaa gataccgcgg     480
ggcaacaccc cctcggaatg aactccaact ttggcgatgt tttcgtggag aaaggcaagt     540
ctttgctcga ccgtgtttct gaggttgtga gcgagtcgtc caagaatatt tccccagaat     600
```

```
tgagggacat tggaatgaa atggaggcca agttcccaga taccctcaga acatgaagc    660 tcaagtcaga gccggcagtc aaaattacaa agaaacctgc cgattttggg acttcaatg    720 ttctcaatga gaagttctcc aactacaagc tgagggttaa aagaccgac ccggagcat    780 tgggactgga ccacacaaga cagtactctg gatacttgga tgtggaggac gaagacaagc    840
atttcttcta ttggatgttt gagtccagaa atgacccggt caacgaccct gtgattctgt    900
ggctcaacgg tggtccagga tgctcttcct tgactggaat gcttttgag ctcggctctg    960 cttctatcgg tccagatctc aagccaatca acaacccata ttcgtggaat tccaatgcca    1020
ctgtgatttt ccttgaccag cctgtcaatg ttggattctc gtactcttcc aagtctgttt    1080
ctaacacggt cgcagctggt aaagacgtct atgctttctt ggagttgttc taccagcaat    1140
tcccacactt gctgaagaac gacttccaca tcgccggcga gtcgtacggt ggtcattaca    1200
tcccagtgtt tgcctccgag attctcaccc atgctgacag atctttcaac ctcacttcgg    1260
tgttgattgg taacggtttg accgacccac ttaaccagta cccattctac gagagaatgg    1320
catgctctac tgatggtggc tatgagcaac cctggacgag tctgagtgcg aaggaatgtt    1380
tggagacctt gcctagatgt ttgtcattga ttgaatcatg ctacagctcg cagtctgtgt    1440
tctcatgtgt cccggcctcc atctactgca acaacgcaca acttggacca ttccaaaaga    1500
ccggcagaaa cgtctacgac gttagaaaga tgtgcgaggg aactctgtgc tacaaagaca    1560
tggaatacat tgaccaatat ttgaaccagg actttgtcaa ggaaaaggtt ggcgctgagg    1620
ttgacactta cgagtcgtgt aatttcgacg tgaacagaaa cttcctgttt gctggtgatt    1680
ggatgaaacc ttaccacaag aacgttatca atctgctgga gcaaggtctt cctgtcctga    1740
tttacgcagg agacaaggat ttcatctgca attggctcgg aaaccaagcc tggtccaatg    1800
agctcccttg gtctggacac gatgaattcg agtcccccga gctgtacaac ctcaccttga    1860
aggatggcac taaggtcggc gaggtcaaga atgctgcaa gttcaccttt gctagaatgt    1920
ttgatggagg acacatggtt ccatacgacc agcctgagag ctctttggct atggtcaata    1980
gatggatagc tggtgactac tccttgggaa ccaagaaata aaaagctcat gaaaacatta    2040
tgtcattgtt gttcaactta tgtatgattg tttgttaaga tacactatct aaattcctcg    2100
ttcaataccc agccttttccg ttccttgtcc catttacata ttgatttgag catcgatcgc    2160
acaaccttga ctgttttttc gtttgagacg tcaatcttca gctcgtcaag aactgcag    2218
```

```
<210> SEQ ID NO 2
<211> LENGTH: 2107
<212> TYPE: DNA
<213> ORGANISM: Hansenula polymorpha DL1
<300> PUBLICATION INFORMATION:
<308> DATABASE ACCESSION NUMBER: U67173
<309> DATABASE ENTRY DATE: 1996-08-17
<313> RELEVANT RESIDUES: (1)..(2107)

<400> SEQUENCE: 2
```

```
gagctcagct acctttggg agccatggca cggtggcctt gattgtacgt tgctcctgca    60
atggtacaaa tgggattaca acaaaggtac cgtcaaatct cccgaaatag aagcacccgc    120
gatgagaaga gaaagtatat ctgcggagaa ttacatcaaa ctgaaaaagt caaagtcgcc    180
tgccacaggg tcagcattca ttaaaatccc aatgtccccg catcacgttc gcaagctgag    240
tgaaaacacg ccactgtcgc ctatcgactt tcttctggac gactatatgg cgaaccacaa    300 cttttacaagg gcaaaaaaca gttcgatgag gttttgaagc tgtcaaacta cggatcgata    360
```

-continued

```
tcttaatcag atcacttgcc tattctggaa gccgcaccag tactagttgg gatagcgtaa    420
atgctcaaaa ctgatgtgtt tatgtgtgac gcactaccta aaatatgagg gtggcaaaga    480
gagtaaaatt tggggttcat taagtaggtt ccataattta caaacctgtt ctgaatagag    540
agtcaccaat ccagttgccc caaaaccttg tcaaaatcat tagcatcgtg agcatctatt    600
ataaacaaag cgaatctcaa agatgaaact ctctttccca acctttact cgcttgctct     660 tgtgcttgga ttggtctccc tggccgatgc caaggtccac aaagctccca tcaaaaaagc    720
tcctgcacag gctacttacc aggatgttac tgtcggcgat tatgttgagt cgttgaagca    780
aaagtatgtt acaacttaca acaagtttat cgccgcccaa cagaatgacc agcaaattat    840
ctcgatcggc aagcgttctg acgagagtgc aagctcgggt cacaacactc ctttgaccaa    900
ctatctcaat gcccaatact tcaccgagat tcaattgggc actcctggcc aatcgttcaa    960
ggttatcctc gacaccggtt cctctaacct gtgggttcct agtagcgatt gcacgtcctt   1020
ggcctgttac ttgcatacta aatacgacca cgatgagtcg tccacttacc agaagaacgg   1080
ttcttcgttt gctattcaat atggctcggg ttccctcgag ggttacgttt cccaagacac   1140
actgactatt ggtgaccttg tcatccctaa acaggatttc gccgaggcta ctagcgagcc   1200
tggcttggct tttgctttg gaaagtttga cggtattctg ggtctggctt acgacacgat    1260
ctcggtcaac agaatcgttc ctccaattta caatgctatc aatttgggat tgctggacac   1320
cccacaattc ggattttacc ttggtgacac ttcgaagtcc gagcaggatg gaggagaggc   1380
tacctttggt ggatacgatg tgtctaagta cacaggcgat atcacctggt tgccagtcag   1440
aagaaaggct tattgggaag tgaagtttag tggtatgccc ttggtgacga atacgctcca   1500
ttggagaaca ccgggagctg ccattgatac cggaaccttct ttgattgctc ttccatctca   1560
attggctgag attttgaact ctcaaattgg tgccgagaag tcatggtctg acagtacca    1620 gatcgattgt gacaagagag actcactgcc tgacctcact ttcaacttcg atggttacaa   1680 cttttaccatc tcgccttatg actacacttt ggaagtttct ggttcttgta tttctgcatt   1740
cactccaatg gacctcccag ccccaattgg tccaatggcc atcattggtg acgctttcct   1800
cagaagatac tactctgtct atgaccttgg cagagacgct gtcggattgg ctaaggctgt   1860
gtaatgcaag gcagttacgt attagtttca acttgctagc atgaatttct atcgggtacg   1920
gttgcttgac aacgattttc tttgtgtctc tattactgct ataaacatg aaaagattgg    1980 atttttttga cagtttctag taattgctta aatctgctct tttcctttg ttgatcccgt    2040 gctgctctgt gtgcttcctt tttttatcta tattattaga ttgtctcttc tttagcagcg   2100
gaagctt                                                             2107
```

<210> SEQ ID NO 3
<211> LENGTH: 3550
<212> TYPE: DNA
<213> ORGANISM: Hansenula polymorpha DL1

<400> SEQUENCE: 3

```
gaattctata ggaatggtgc aaaacgaagg atcgtgtgga ctcatgaatg tgctatattt     60
gtggctaaaa agcctgccag agctcgcagg agataagagg tctggcgtcg tgctgcgcaa    120
aatgatcgcc ttgataaaat tcctcaatct cgatcatgaa tcagggttca agtatttttgg   180 ttttttcttt caagacgagt atgaactgga acacgctctc gagtcctaga cgaccaggac   240
atcaagcagg cggccgcact cgaagatctc gccgcttttg atttccaaca ctttgacgtc   300
gtggaggttg accagaccct tttcgatgcc tatgagctcg agctcggtct cgaacaggtt   360
```

-continued

```
tcctgggtct aacgtgaatt tcaggttgtt ggtaagagaa atcagcccca ctttgctgaa    420
ctcgtgttgg aaagcccgca ccagctggtt gaggccgtaa agcgggacgg atctgcctt     480
gttgcgttc tggatcggaa ttggtggcac agattttcg tattgtttgt tgatcgatga      540
ttgaatgtac agtatgagcg ataacgagtc gttcgacttg ttgataaatt gtagcttcca    600
tttgaacacc tcgccgagct tgactttagt ctggcccgaa actgaaatgc tgaggttctt    660
cttggagtgg ttgagagtca ccgacgagtt ggatcgtagt ttattttct taggcaaatt    720
cagagcagag ttggtcgact tggatttaaa taccccgaga ctaggcgacg cgattggggg    780
cacggtgggg gccgccataa aatccacatt tgtagtccat cgtgtcacga ttttctatt    840
cccgttgacc gtgcaatgga tggtgacaaa aaccggctta acccacttga tgtcgttgtt    900
tgttagtctg tacgtgagcg acagaataga atggttctgc aacaccaatg gatactttac    960
caccgagtag ccggcacaca gacagtttct gatgtccata tctaccgact cgattctcac   1020
cgacacttct gacgcccgga cctgtccaga aagagccact tccaaagagg ccatggtttt    1080
ctccgtcttg atggtcttga accgcatctg aatacggggg ctgatccgca gcgacgtgtc    1140
ggccgttacg agttcgtaaa ggtccacatg cttcgtcagc acagtgttgc ctatagtgac    1200
tgtatcctgc aactctaaat tttctatctt tctcgactgt tgtcgaaacg aggctttgat   1260
ctgcaattga tttgaaagtt tgtcaggcac acggtcgtt tccagtatcc atacggcctc    1320
agaccctatg acgactttgg aatcgagcac ttttctcgct gtgttttgca agttgtatac    1380
caggtcgacc tcgacctgtg tcacagacga cggagtgtac accacgactt ggatgtcctc    1440
gtcgaaatag gcaatgtcca gcgtgtcgca ctggcgcagc tgttccacgg agcccagcac    1500
atcagcagaa acccgggttt tcggaacaag cacaccaaac attggaaaca acacttatcg    1560
acgcgggtgt gtttaaaaaa taatattaga tcgactgctc ctactctttt aaattcttta    1620
tttatcccag gctagacag cacagagcta accatgagtc ggtatttttt actagcgtgc     1680
acattggctc tgcaatgtgt cgcggcctcc caggaggact acatagtcaa ggatttgcct    1740
ggactctcga atattcctgc cgtggtgagg ccagtgatgc atgccggaca ccttgaaata    1800
gatgaggaac acaacaccga gctgttttc tggcgattcc agaatccgaa gaacaacggg     1860
acacaccaaa cgctccaccg caatgagctg atcgtctggc tgaacggtgg ccctggctgc    1920
tcgtcgatgg atggagccat gatggaaaca ggccccctgc gggtgtcaga caagttggag    1980
gtggagctca acccgggatc ctggacacag gtggccgata tcttgtttgt ggatcagccg    2040
gccggaattt tgagaaagtg gagtgcgtca aaatattcca tagtatttg gctgccagta    2100
gagacgaaac caagcctgcc aaagaacaat gtgtcaacat gtacgactac cgcaaacatg    2160
attacttccc tgcatgcgga tccaattggc cagaaggcct gcccaccgtg actaaatttc    2220
tgaatctgga tgctgtgcaa aaagccctga acctgaaatc ggcgaagaga tggcacgagt    2280
gtgacggaaa agtcgaattc ttttttccagc cagagcactc tgtcaagtcg ttcgacctgc    2340
tgccaaaact actggagaaa atgaaaatcg cgctgtttgc tggcgacaag gacattatct    2400
gcaaccacaa atcaatagaa atggtgattg aaaaattgca aattacacca ggacaattcg    2460
gtttcacaaa cagcagaaag tctggctgga tctacgacgg gcaggaagtg ggtgaggttg    2520
agacacagtc gaacctcacg tatatcaagg tgttcaattc gtcgcatatg gtgccttacg    2580
acctgccgga ggtgagcaga ggactattcg atataatcac aaactctatt gaaaaacggt    2640
cgacagacat tgtgacgccc gtttatgaca gcagaggcaa ctacaagttt gtggaggaga    2700
```

```
agcaggacac cgaccagaac gaggaagaag agaaggagaa acctcccaag caccatcata      2760
gtctcacgtt ttacgtggca gaggtggcga ttctggcagt gctagcatat ctgctttaca      2820
gcttctacaa atcgttcgcc aaatcgcgta agtctgcatt tttgtcactc tcttccaaga      2880
agaagaagaa gcaggtgcac tggtttgacg agagcgacta aggaatggac caggaagctg      2940
gcgaggcaga tcataagcct aagagcatgc tggagtcggt gttcaacaag ctgggctatg      3000
gaggacagta tgacacggta caggacggcc gtgacatcga gatggcgccg gtcgaagaac      3060
acgaagacca atttattatt caaagcgacg aggaagagtt tggccacaga tagagtacga      3120
ttatataata tccacgaaaa attagtttcc aattatttcg ctcctgattg taatgtctca      3180
aagttggatc ctctggaagc ggtccctgat taccggcggt ggaattattg gaagcggtgt      3240
gctactgtac aaattcacga ctcctaccga ggaacagttg atcgctaaat tatccccga      3300 gctgagagca gactatgaac gcaacaaaga attgcggagg aaagaacagg agatgttgat      3360
ggagatcgtc aaacgacgg cagcgtcgaa cgatccggtg tggaagacag ggccgattgt      3420
gtcgccgtgg gaccgggact ttacgccatc gagggaaagt ttattagtga agagagagcg      3480
atttgagaaa gagcaggcgg agaaaaaaca gcgcgaagag ctcgagcgtc tgaaagccga      3540
ggccaagctt                                                             3550
```

```
<210> SEQ ID NO 4
<211> LENGTH: 17
<212> TYPE: DNA
<213> ORGANISM: Artificial Sequence
<220> FEATURE:
<223> OTHER INFORMATION: PCR primer for S. cerevisiae PRC1 gene

<400> SEQUENCE: 4
atgaaagcat tcaccag                                                     17

<210> SEQ ID NO 5
<211> LENGTH: 17
<212> TYPE: DNA
<213> ORGANISM: Artificial Sequence
<220> FEATURE:
<223> OTHER INFORMATION: PCR primer for S. cerevisiae PRC1 gene

<400> SEQUENCE: 5
ttataaggag aaaccac                                                     17

<210> SEQ ID NO 6
<211> LENGTH: 17
<212> TYPE: DNA
<213> ORGANISM: Artificial Sequence
<220> FEATURE:
<223> OTHER INFORMATION: PCR Primer for S. cerevisiaae PEP4

<400> SEQUENCE: 6
atgttcagct tgaaagc                                                     17

<210> SEQ ID NO 7
<211> LENGTH: 16
<212> TYPE: DNA
<213> ORGANISM: Artificial Sequence
<220> FEATURE:
<223> OTHER INFORMATION: PCR primer for S. cerevisiae

<400> SEQUENCE: 7
tcaaattcgt ttggcc                                                      16
```

```
<210> SEQ ID NO 8
<211> LENGTH: 27
<212> TYPE: DNA
<213> ORGANISM: Artificial Sequence
<220> FEATURE:
<223> OTHER INFORMATION: PCR primer for H. polymorpha KEX1

<400> SEQUENCE: 8
tggytsaacg ghccwgghtg ytcbtcb                                27

<210> SEQ ID NO 9
<211> LENGTH: 30
<212> TYPE: DNA
<213> ORGANISM: Artificial Sequence
<220> FEATURE:
<223> OTHER INFORMATION: PCR primer for H.polymorpha KEX1

<400> SEQUENCE: 9
wggratgtay tgwccrgcgt avgactcdcc                             30

<210> SEQ ID NO 10
<211> LENGTH: 5
<212> TYPE: PRT
<213> ORGANISM: Human
<220> FEATURE:
<223> OTHER INFORMATION: N-terminal hEGF

<400> SEQUENCE: 10

Asn Ser Asp Ser Glu
 1               5

<210> SEQ ID NO 11
<211> LENGTH: 5
<212> TYPE: PRT
<213> ORGANISM: Human
<220> FEATURE:
<223> OTHER INFORMATION: C-terminal hEGF

<400> SEQUENCE: 11

Trp Trp Glu Leu Arg
 1               5
```

HANSENULA POLYMORPHA MUTANTS AND PROCESS FOR THE PREPARATION OF RECOMBINANT PROTEINS USING THE SAME

This application is a divisional of application U.S. Ser. No. 09/674,617, filed Jan. 3, 2001, now abandoned, from which priority is indicated herein under 35 USC § 371 PCT/KR00/00173, filed Mar. 4, 2000 (International Publication No. WO 00/52113, published in English on Sep. 8, 2000) and Republic of Korea application 10743, filed Mar. 3, 2000, and Republic of Korea application 7177, filed Mar. 4, 1999.

TECHNICAL FIELD

The present invention relates to *Hansenula polymorpha* mutants and a process for preparing recombinant proteins using them. More particularly, the present invention relates to *Hansenula polymorpha* mutants useful as host cells through which various proteins can be produced as being intact at high yield and to a preparing process of recombinant proteins using the same.

BACKGROUND ART

Gene recombination technology, which has been recently developed with a great advance, allows the mass production of the proteins which are derived from higher organisms by introducing the genes of interest into microorganisms. Largely, of interest are the proteins that are medicinally useful because they are of high value. Demand for proteinaceous medicines of high purity is expected to increase explosively as there continue to be discovered diseases that are intractable, but curable with such proteinaceous medicines. Thus, there are needed techniques in which functional recombinant proteins can be produced at relatively low costs through various microorganisms harmless to the body.

Yeast, a microorganism which performs protein expression and secretion like an eucaryote, is usefully utilized as a host through which recombinant proteins derived from higher organisms can be produced on a large scale. Typically, *Saccharomyces cerevisiae* is used as such a host in the study on recombinant protein production using yeast. However, the strain is now regarded unsuitable in the following aspects: recombinant proteins are produced in low yields on account of not only the absence of a strong promoter for the effective expression of exogenous proteins, but also the instability of the plasmids introduced into the yeast upon long-term fermentation; there is needed fed-batch fermentation when the strain is cultured at a high concentration; and expressed exogenous proteins undergo hyperglycosylation (Romanos, et al., *Yeast*, 8: 423 (1992)). An exogenous protein expression system to overcome the above problems was developed in *Pichia pastoris*, a methanol-assimilating yeast (Sudbery et al., *Yeast*, 10: 1707 (1994); Cregg et al., *Bio/Technol.* 5: 479 (1987)). In addition, active research has been directed to the development of exogenous protein expression systems using *Hansenula polymorpha*, a methanol assimilating yeast (Gellissen et al., *Bio/Technol.* 9: 291 (1991); Janowicz et al., *Yeast* 7: 431 (1991)). *Hansenula polymorpha*, which is gathering strength as a novel host cell for producing recombinant proteins, utilizes methanol as a carbon source and thus, can be mass-cultured with ease. In addition, this yeast strain contains a strong promoter for several genes relevant to its methanol metabolism and allows the multicopy integration of exogenous genes into its genomic DNA so that the plasmids can be stably maintained even when it is cultured at high concentrations.

In the case that recombinant proteins are produced by use of yeast, not only is an effective expression and secretion system necessary for the enhancement of the yield, but it is very important to prevent proteinases from degrading the exogenous proteins expressed and secreted. Usually, the culture of recombinant yeasts for a long period of time in a fermentation bath suffers from a problem in that proteinases secreted from the host cells to the media naturally or through cell lysis degrade the produced recombinant proteins to lower the production yield of the recombinant proteins. In fact, analysis through, for example, HPLC and MS demonstrated that a substantial part of the recombinant proteins, such as human epidermal growth factor secreted from recombinant *Saccharomyces cerevisiae*(George-Nascimento et al., *Biochemistry* 27:797(1988)) and *Pichia pastoris*(Clare et al., *Gene* 105:205(1991)) cells to their culture media were degraded at their carboxyl ends. It was postulated that carboxypeptidases of the host cells removed one or two amino acids from the carboxyl ends of the recombinant proteins secreted.

Corresponding to the lysosomes of higher cells, the vacuoles of *Saccharomyces cerevisiae* contain various proteinases and are responsible for proteolysis upon depletion of nutrition. Particularly, carboxypeptidase Y is utilized for the carboxyl-terminal amino acid analysis by virtue of its capacity of hydrolyzing various protein substrates and is a model protein under active and extensive study on protein sorting and targeting (Rothman et al., *Cell*, 47: 1041 (1986); Johnson et al., *Cell*, 48: 875 (1987); Valls et al.,*J. Cell. Biol.*, 111:361 (1992)). In addition, the carboxyl-terminal degradation which takes place upon the over-expression of exogenous proteins is also known to be due to carboxypeptidase Y. Carboxypeptidase Y genes are reported to be cloned from *Saccharomyces cerevisiae, Candida albicans, Pichia pastoris*, and *Schizosaccharomyces pombe* (Valls et al., *Cell*, 48: 887 (1987); Mukhtar et al., *Gene*, 121: 173 (1992); Ohi et al., *Yeast*, 12: 31 (1996); Tabuchi et al.,*J. Bacteriol.*, 179: 4179 (1997)).

Along with carboxypeptidase Y, *Saccharomyces cerevisiae* protease A is present within vacuoles, playing a role in hydrolyzing proteins. Further, protease A takes part in the proteolytic process of vacuolar proteases, such as protease B, carboxypeptidase Y and aminopeptidase Y, as well as vacuolar hydrolases, such as RNase, alkaline phosphatase, and acid trehalase (H. B. Van Den Hasel et al., *Yeast*, 12: 1 (1996)). Particularly in the strains whose gene PEP4 is disrupted, the activity of carboxypeptidase Y is significantly reduced. Accordingly, since the activity of carboxypeptidase Y is significantly lowered in a *Hansenula polymorpha* whose PEP4 gene is disrupted, the disruption of the PEP4 gene on the genome can make various lyases, including carboxypeptidase Y, low in enzymatic activity. Gene PEP4 is cloned from *Saccharomyces cerevisiae, Candida albicans*, and *Neurospora crassa* as disclosed in several documents (Ammerer et al., Mol, Cell. Biol., 6: 2490 (1986); Woolford et al., Mol. Cell. Biol., 6: 25 (1986); Lott et al., Nucleic Acids Res., 17: 1776 (1986); Bowman et al., Genbank Accession No U36471).

The gene KEX1 of yeast is known to code for carboxypeptidase a that is involved in the processing of killer toxins K1 and K2 and an α-factor (mating pheromone) precursor (Alexander et al., Cell, 50: 573 (1987)). Carboxypeptidase α is a digestive enzyme that hydrolyzes the carboxyl-terminal peptide bond in polypeptide chains. Hydrolysis had been known to occur most specifically if the carboxyl-terminal residue is a basic amino acid such as arginine or lysine. However, expression of hirudin, a thrombin inhibitor, in *Saccharomyces cerevisiae* demonstrated that the specificity of carboxypeptidase α is not confined to basic amino acids, but extended further to non-basic amino acid, such as tyrosine, leucine and glutamine, at the carboxyl end (Hinnen et al., *Gene Expression in Recombinant Microorganism*, 155: 164 (1994)).

Expression systems for *Pichia pastoris* in use were usually developed by introducing in the microorganism truncated expression vectors which were then allowed to be inserted at the site of gene AOX1 or HIS4 through homologous recombination. When an expression cassette composed of an AOX1 promoter and a terminator is inserted to the site of gene AOX1, disruption occurs in the gene AOX1, creating an aox1 transformant. While the normal strain produces a large quantity of AOX1 enzyme upon methanol culture, the aox1 strain cannot produce the AOX1 enzyme any more, exhibiting a very slow growth rate (methanol utilization slow: Mud). Hence, this mutant has an advantage over the AOX1 wild type (Mut$^+$) in that the mutant can be grown in an even sparser oxygen atmosphere than the wild type can. There are several reports which reveal the superiority of the Mut$^S$ recombinant strain to the Mut$^+$ strain in recombinant protein production yield through the fermentation by use of the Mut$^S$ recombinant strain and the Mut$^+$ strain, indicating that the Mut$^S$ strain is more useful for the mass production of some recombinant protein (Cregg et al., Bio/Technology 5: 479 (1987); Romanos et al., Vaccine 9: 901 (1991)).

In contrast, conventional expression systems for *Hansenula polymorpha* were developed by taking advantage of the phenomenon that a multicopy of an exogenous gene is tandemly introduced to non-specific sites of the genome. Accordingly, intact expression vectors, which are not cut, but circular, are introduced into the host (Janowicz et al., *Yeast*, 7: 431 (1991); Gelalissen et al., *Trends Biotechnol*. 10: 413 (1992); Gatzke et al., *Appl. Microbiol. Biotechnol*. 43: 844 (1995)). In this case, the conventional expression systems suffer from a significant problem in that, because different expression efficiencies appear depending on the host genome sites to which the expression vectors are inserted, there is needed the consumptive searching procedure of analyzing expression yields of numerous transformants to select the transformant which is the most productive of the recombinant protein of interest. In addition, unlike the Pichia pastoris expression system which is high in homologous recombination frequency, *Hansenula polymorpha* systems, even though utilizing an MOX promoter and an MOX terminator, make exogenous genes inserted, for the most part, to non-specific sites of the host genome. Further, even when the exogenous gene is inserted to the MOX gene site at a low frequency, the vector is incorporated as being intact, so that the MOX genes of the transformants are not damaged. In methanol culture media, these MOX transformants, to experimenters' disappointment, show poorer expression yields for the recombinant protein of interest than expected because most of the methanol fed is consumed as the substrate of the MOX enzyme which is of high activity (Kim et al., Biotechnol Lett. 18:417 (1996)). In the MOX wild types cultured in methanol, moreover, the expressed MOX protein amounts to as much as 30–40% of the total expressed proteins (Guiseppin et al., Biotechnol. Bioeng. 32:577 (1988)), resulting in relatively reducing the expression efficiency of the recombinant protein of interest.

For *Hansenula polymorpha*, there have been not yet developed techniques by which expression cassettes inserted in the host genome can be rendered to pop out later. Thence, as indicated in the report of Hodgkins et al. (Hodgkins et al., *Yeast* 9:625), even after a desired mutant is obtained by using as a mother strain a transformant carrying an expression cassette for a particular recombinant protein, the mutant, which is obtained under difficulties, cannot be used as a general host to express various recombinant proteins because of the incapability of popping out the preexisting expression vector from the host genome and thus of introducing a new expression cassette into the host genome.

DISCLOSURE OF THE INVENTION

In order to produce whole recombinant proteins in *Hansenula polymorpha*, there are developed *Hansenula polymorpha* mutant strains that are deficient in proteases. To begin with, the genes PRC1, KEX1 and PEP4 which code for carboxypeptidase Y, carboxypeptidase α and protease A, respectively are cloned. By taking advantage of these cloned genes, a carboxypeptidase Y-deficient mutant strain, a carboxypeptidase α-deficient mutant strain, a protease A-deficient mutant, and multi-phenotype deficient mutant strains are developed. The exogenous proteins produced from these mutant strains show a remarkable decrease in the amino acid degradation in their carboxyl terminal regions. In the invention, *Sacchromyces cerevisiae* genes are utilized to clone the genes of interest from *Hansenula polymorpha*. The *Sacchromyces cerevisiae* carboxypeptidase Y gene (PRC1) is obtained by PCR and used as a probe to detect the *Hansenula polymorpha* PRC1 by Southern blotting. The genome of *Hansenula polymorpha* DL-1 is digested with various restriction enzymes and repetitively subjected to Southern blotting, so as to determine the base sequence of the *Hansenula polymorpha* PRC1. This procedure can be applied to determine the base sequence of the gene PEP4 coding for the protease A of *Hansenula polymorpha* DL-1. For the cloning of *Hansenula polymorpha* KEX1 gene, primers are synthesized on the basis of a high homology region among strains and used to amplify a portion of the KEX1 gene by PCR with the *Hansenula polymorpha* genome serving as a template. The PCR product is used as a probe for Southern blotting to clone the whole KEX1 gene of *Hansenula polymorpha*.

A *Hansenula polymorpha* LEU2 gene is inserted into plasmids pHDY2 and pHDP4 to construct plasmid pHYL and pHPL, respectively. With the constructed plasmids pHYL and pHPL, *Hansenula polymorpha* UR2 is transformed into a carboxypeptidase Y mutant and a protease A mutant, respectively. Investigation of the carboxypeptidase activity of these mutants and Southern blotting analysis identify the disruption of the *Hansenula polymorpha* PRC1 and PEP4 genes.

In order to disrupt the KEX1 gene of *Hansenula polymorpha* DL1 strain, plasmid pKUZ is constructed by inserting a *Hansenula polymorpha* URA3 gene pop-out cassette into plasmid pKH3.9 and used to transform the *Hansenula polymorpha* DL1 strain into a carboxypeptidase a mutant strain. Selection is made on a *Hansenula polymorpha* URA43 gene pop-out strain whose genome, together with the genome of the wild type, is then subjected to Southern blotting to identify the disruption of the KEX1 gene. In addition, the genes PRC1 and PEP4 of *Hansenula polymorpha* DL 1 strain are both disrupted. In this regard, a *Hansenula polymorpha* UP43 gene pop-out cassette is inserted into plasmids pHDY2 and pHDP4 to construct plasmids pHTUZ and pHPUZ, respectively. As in the KEX1 gene disruption, transformation and popping out are repeated to prepare a protease A/carboxypeptidase α mutant, a protease A/carboxypeptidase Y mutant, a carboxypeptidase α/carboxypeptidase Y mutant, and a protease A/carboxypeptidase α/carboxypeptidase Y mutant.

In the invention, there is also constructed a vector which can disrupt a MOX gene coding for methanol oxidase, a first enzyme in the methanol metabolism of methanol-assimilating *Hansenula polymorpha*, and a TRP3 gene adjacent to the MOX gene, at once. This vector is used to prepare a novel mutant DLT2 whose MOX gene is disrupted. The novel mutant DLT2 can serve as a host through which recombinant proteins of interest can be produced at high yield without continuous feeding of methanol, with the aid of an expression cassette carrying a promoter capable of inducing the expression at a low concentration of methanol. Further, there is developed a pop-out technique in which a recombinant protein expression cassette is inserted into a MOX gene site of the mutant and is allowed to pop out therefrom, thereby utilizing the mutant as a host for general use in producing various proteins of interest.

Therefore, it is an object of the present invention to provide gene base sequences coding for carboxypeptidase Y, carboxypeptidase α and protease A, respectively, derived from *Hansenula polymorpha*.

It is another object of the present invention to provide mutant strains deficient in carboxypeptidase Y, carboxypeptidase α, protease A and combinations thereof, which are transformed from *Hansenula polymorpha* by use of vectors which contain a disrupted PRC1 gene coding for carboxypeptidase Y, a disrupted KEX1 gene coding for carboxypeptidase α, a disrupted PEP4 gene coding for protease A, and combinations thereof.

It is a further object of the present invention to provide a process for producing recombinant proteins, in which the protease mutant strains are utilized as host cells to produce the recombinant proteins without degradation at carboxyl terminal.

It is still a further object of the present invention to provide a process for producing recombinant proteins at high yield, in which a *Hansenula polymorpha* mutant, deprived of methanol assimilating ability and incapable of utilizing methanol as a carbon source, is used as a high yield host to produce recombinant proteins without continuous feeding of methanol, with the aid of an expression cassette carrying a promoter capable of inducing the expression at a low concentration of methanol.

It is still another object of the present invention to provide a pop-out technique in which a recombinant protein expression cassette is inserted into a MOX gene site of the mutant and is allowed to pop out therefrom, thereby utilizing the mutant as a host for general use in producing various proteins of interest.

BRIEF DESCRIPTION OF THE DRAWINGS

The above and other objects, features and other advantages of the present invention will be more clearly understood from the following detailed description taken in conjunction with the accompanying drawings, in which:

FIG. 9 shows the results of Southern blotting for confirming the disruption of genes of interest;

FIG. 12 shows MOX wild type and Δmox mutant DLT2 strain which are grown on various media containing dextrose or methanol as a main carbon source;

BEST MODES FOR CARRYING OUT THE INVENTION

Figure 1:
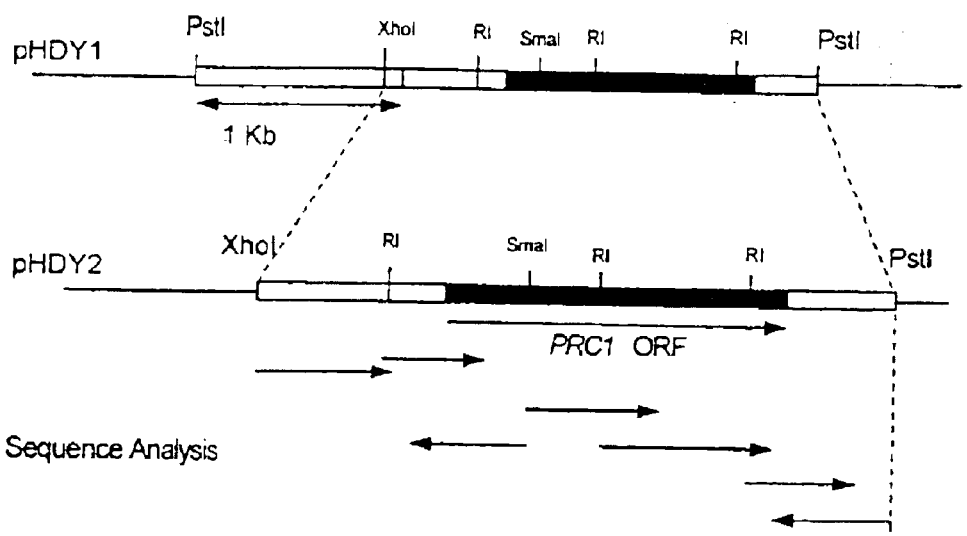
FIG. 1 is a restriction map of a *Hansenula polymorpha* PRC1 gene.

A *Sacchromyces cerevisiae* carboxypeptidase Y gene (PRC1) is amplified by PCR. This PCR product is used as a probe in detecting a corresponding *Hansenula polymorpha* gene (PRC1) through Southern blotting. First, the genome of *Hansenula polymorpha* DL-1 is treated with restriction enzymes and hybridized with the probe. A DNA band is detected from a 3 kb PstI DNA fragment which is, then, inserted into a plasmid for preparing a DNA library. After extensive Southern blotting processes, a plasmid carrying a *Hansenula polymorpha* PRC1 gene was selected. After the DNA fragment is reduced into a 2.2 kb XhoI/PstI fragment which is then used to construct plasmid pHDY2. The base sequence of the gene is read as given in SEQ ID NO: 1.

Based on a well known *Sacchromyces cerevisiae* PEP4 gene, a set of two primers is synthesized. After being amplified by PCR with the aid of the primers, the *Sacchromyces cerevisiae* PEP4 gene fragment is used as a probe for Southern blotting. First, the genome of *Hansenula polymorpha* DL-1 is treated with restriction enzymes and hybridized with the probe. A DNA band is detected from a 8 kb BamHI DNA fragment which is, then, inserted into a plasmid for preparing a DNA library. After extensive Southern blotting processes, a plasmid carrying a *Hansenula polymorpha* PEP4 gene was selected.

Well-known amino acid sequences of carboxypeptidase α of many strains are analyzed to select high homology regions. On the basis of the amino acid sequences of the high homology regions, primers are designed. A PCR using the primers resulted in the amplification of a KEX1 DNA fragment 306 bp long, from the *Hansenula polymorpha* DL-1 genome. This PCR product is used as a probe in detecting a whole *Hansenula polymorpha* gene KEX1 through Southern blotting. First, the genome of *Hansenula polymorpha* DL-1 is treated with restriction enzymes and hybridized with the probe. A DNA band is detected from a 4.5 kb HindIII DNA fragment which is, then, inserted into a plasmid for preparing a DNA library. After extensive Southern blotting processes, a plasmid carrying a *Hansenula polymorpha* KEX1 gene was selected. After the DNA fragment is reduced into a 3.9 kb EcoRI/HindIII fragment which is then used to construct plasmid pKH3.9. The base sequence of the gene is read as given in SEQ ID NO: 3.

The cloned carboxypeptidase Y gene (PRC1) and protease A gene (PEP4) are utilized to disrupt their corresponding genes on the genome of *Hansenula polymorpha* DL-1. To this end, a *Hansenula polymorpha* LEU2 gene is inserted into plasmids pHDY2 and pHDP4 to construct pHYL and pHPL, respectively. Using these plasmids, a *Hansenula polymorpha* UR2 strain (leu2, hEGF, PRC1, PEP4, KEX1) is transformed into a carboxypeptidase mutant strain (hEGF, prc1::LEU2, PEP4, KEX1) and a protease mutant strain (hEGF, pep4::LEU2, PRC1, KEX1), respectively. The disruption of the genes of interest can be confirmed by analyzing the resulting mutants for the activity of the carboxypeptidase Y and by genomic Southern hydridization between the mutants and the wild type.

For the muti-disruption of KEX1, PEP4 and PRC1 genes, a *Hansenula polymorpha* URA3 gene pop-out cassette is introduced into plasmid pKE3.9, pHDY, pHDP4 to construct plasmids pKUZ, pHYUZ, and pHPUZ, respectively. With the plasmid pKUZ, a *Hansenula polymorpha* DL1 strain (leu2, ura3, KEX1, PEP4, PRC1) is transformed into a carboxypeptidase α mutant strain (leu2, kex1::URPA3, PEP4, PRC1), followed by popping the URA3 gene out. Likewise, the plasmids pHYUZ and pHPUZ are used to prepare a carboxypeptidase Y mutant strain and a protease A mutant strain, respectively. The disruption of the genes of interest can be confirmed by genomic Southern hydridization between the mutants and the wild type.

The recombinant protein of interest, for example, hEGF is expressed in the carboxypeptidase Y/protease A mutant strain. This protein can be obtained with ease by attaching a signal peptide to the protein. In this case, the recombinant protein can be obtained only by centrifugation of the cell culture. HPLC analysis is useful to determine whether the recombinant protein is degraded at its carboxyl terminal.

Also, in an embodiment of the present invention, there is provided a process for producing recombinant proteins by use of a *Hansenula polymorpha* mutant strain whose methanol oxidase gene (MOA) is disrupted. In the process, a vector for disrupting the MOX gene and its neighboring TRP3 gene on the genome of *Hansenula polymorpha* is constructed and introduced into the host to prepare a Δmox mutant. In this mutant, an recombinant protein expression cassette can be inserted into or popped out from the genome. Culturing the Δmox mutant harboring a gene of interest in a methanol medium results in producing the corresponding recombinant protein at high yield. As a vector for disrupting the MOX and TRP3 genes on the genome of *Hansenula polymorpha*, at once, pMLT-delta was developed and deposited in the Korean Collection for Type Culture of Korea Research Institute of Bioscience and Biotechnology (KRJBB) under the accession No. KCTC 0727BP on Feb. 10, 2000. Using this vector, a *Hansenula polymorpha* mutant DLT2 whose genomic MOX and TRP3 genes are disrupted was also developed and deposited in the Korean Collection for Type Culture of Korea Research Institute of Bioscience and Biotechnology under the accession number of KCTC 0728BP on Feb. 10, 2000. The novel mutant DLT2 can serve as a host through which recombinant proteins of interest can be produced at high yield without continuous feeding of methanol, with the aid of an expression cassette carrying a promoter capable of inducing the expression at a low concentration of methanol.

Further, in another embodiment of the present invention, there is provided a pop-out technique in which a recombinant protein expression cassette is inserted into a MOX gene site of the mutant and is allowed to pop out therefrom, thereby utilizing the mutant as a host for general use in producing various proteins of interest.

A better understanding of the present invention may be obtained in light of the following examples which are set forth to illustrate, but are not to be construed to limit the present invention.

EXAMPLE I

Preparation of Protease Gene-Disrupted Mutant of *Hansenula polymorpha*

Experiment I: Isolation of Genes Carboxypeptidase Y-Encoding PRC1, Protease A-Encoding PEP4, and Carboxypeptidase α-Encoding KEX1

First Step: Construction of Probes for Cloning *Hansenula polymorpha* Genes PRC1, PEP4 and KEX1

In order to obtain a Saccharomyces cerevisiae PRC1 gene, there were used the following primers:

Primer C1 (SEQ ID NO:4): 5-ATG AAA GCA TTC ACC AG-3

Primer C2 (SEQ ID NO:5): 5-TTA TAA GGA GAA ACC AC-3

With the aid of the primers C1 and C2, 25 cycles of PCR, each consisting of a denaturing step at 94° C. for 30 sec, an annealing step at 55° C. for 30 sec and an extending step at 72° C. for 2 min, resulted in the acquisition of a *Sacchromyces cerevisiae* PRC1 gene 1.6 kb long while the genomic DNA of *Sacchromyces cerevisiae* served as a template for the enzyme. Using a DIG-labelling and detection kit, commercially available from Boehringer Mannheim, the PCR product was labeled according to the indications of the kit manual to give a probe for cloning a PRC1 gene of *Hansenula polymorpha*.

Synthesized for the amplification of a *Sacchromyces cerevisiae* PEP4 gene were the following primers:

Primer P1 (SEQ ID NO:6): 5-ATG TTC AGC TTG AAA GC-3

Primer P2 (SEQ ID NO:7): 5-TCA AAT TCG TTT GGC C-3

The *Sacchromyces cerevisiae* PEP4 gene 1.22 kb long was obtained from the *Sacchromyces cerevisiae* genomic DNA through 25 cycles of PCR, each consisting of a denaturing step at 94° C. for 30 sec, an annealing step at 55° C. for 30 sec and an extending step at 72° C. for 2 min. This PEP4 gene was labeled in the same manner as in the above *Hansenula polymorpha* PRC1 gene, so as to give a probe for cloning a PEP4 gene of *Hansenula polymorpha*.

As for a probe for detecting a *Hansenula polymorpha* KEX1 gene, it was obtained by PCR using the following primers:

Primer K1 (SEQ ID NO:8):
5-TGG YTS AAC GGH CCW GGH TGY TCB TCB-3

Primer K2 (SEQ ID NO:9):
5-WGG RAT GTA YTG WCC RGC GTA VGA CTC DCC-3

In this regard, five cycles of a PCR, each consisting of a denaturing step at 94° C. for 30 sec, an annealing step at 50° C. for 30 sec and an extending step at 72° C. for 30 sec was conducted, followed by performing 20 cycles of a PCR under the heat condition consisting of a denaturing step at 94° C. for 30 sec, an annealing step at 55° C. for 30 sec and an extending step at 72° C. for 30 min to amplify a *Hansenula polymorpha* KEX1 DNA segment 306 bp. This DNA segment was labeled in the same manner as in the above to prepare a probe for cloning a *Hansenula polymorpha* PRC1 gene.

Second Step: Isolation of Genomic DNA from *Hansenula polymorpha* DL1

From the *Hansenula polymorpha* DL1 cultured in a YEPD medium (peptone 2%, Yeast extract 1%, glucose 2%), genomic DNA was isolated according to the Johnstone's method (Yeast Genetics, molecular aspects, pp. 107–123, IRL Press, 1988).

Third Step: Construction of Plasmid pHDY2

In order to detect a PRC1 gene from the genomic DNA of *Hansenula polymorpha*, Southern blotting was conducted with the probe prepared in the first step. First, after six aliquots of the genomic DNA obtained in the second step were treated with restriction enzymes BamHI, EcoRI, EcoRV, HindIII, PstI, and SalI, respectively, the resulting DNA fragments were fractionated on a 0.9% agarose gel by electrophoresis. The separated DNA molecules were transferred to a Nytran membrane (Schleicher & Schuell) by blotting, followed by exposing the membrane to the labeled probe under conditions favoring hybridization. For this hybridization, a hydrid buffer (5×SSC, 0.1% N-lauryl sarcosine, 0.02% SDS, 2% blocking agent, 30% formamide) was used at 42° C. for 6 hours as indicated in the product manual of Boehringer Mannheim. The membrane was added with an alkaline phosphatase-conjugated antibody and then with BCIP and X-phosphate for color reaction. A band that was dyed blue was observed in a DNA fragment which was cut into a length of about 3 kb by restriction enzyme PstI.

Next, the DNA fragment was isolated from the position at which the blue band appeared, and ligated to plasmid pBluescript KSII+ with which *E. coli* DH5 was transformed to prepare a DNA library. This DNA library was subjected repetitively to Southern blotting to select a plasmid carrying the PRC1 gene, called plasmid pHDY1. Double digestion with restriction enzymes XhoI/PstI reduced the DNA fragment from about 3 kb to about 2.2 kb. The plasmid harboring the XhoI/PstI DNA fragment, was called pHDY2. It was deposited in the Korean Collection for Type Culture (KCTC), placed in Korea Research Institute of Bioscience and Biotechnology (KRIBB), #52, Oun-dong, Yusong-ku, Taejon 305–333, Republic of Korea, on the date of Feb. 18, 2000 and it was accepted under the accession number of KCTC 0732BP. The restriction site mapping and base sequencing of the *Hansenula polymorpha* DL1 PRC1 gene was conducted as illustrated in FIG. 1. The base sequence of the PRC1 gene is given in SEQ ID NO: 1. This DNA sequence was registered as U67174 with GenBank on Aug. 17, 1996. Analysis of the base sequence revealed that the *Hansenula polymorpha* DL1 PRC1 gene is 1,626 bp long with no introns and shows 54% homology to the base sequence of a *Sacchromyces cerevisiae* PRC1 gene. When being deduced from SEQ ID NO:1, the amino acid sequence of the *Hansenula polymorpha* DL1 PRC1 gene exhibits 50% homology to the carboxypeptidase Y of *Sacchromyces cerevisiae*. In addition, high homology can be found in the region around of $263^{rd}$ amino acid reside, which is identified to be a serine acting as a catalytic group within an active site of serine protease.

Fourth Step: Construction of Plasmid pHDP4

Figure 2:
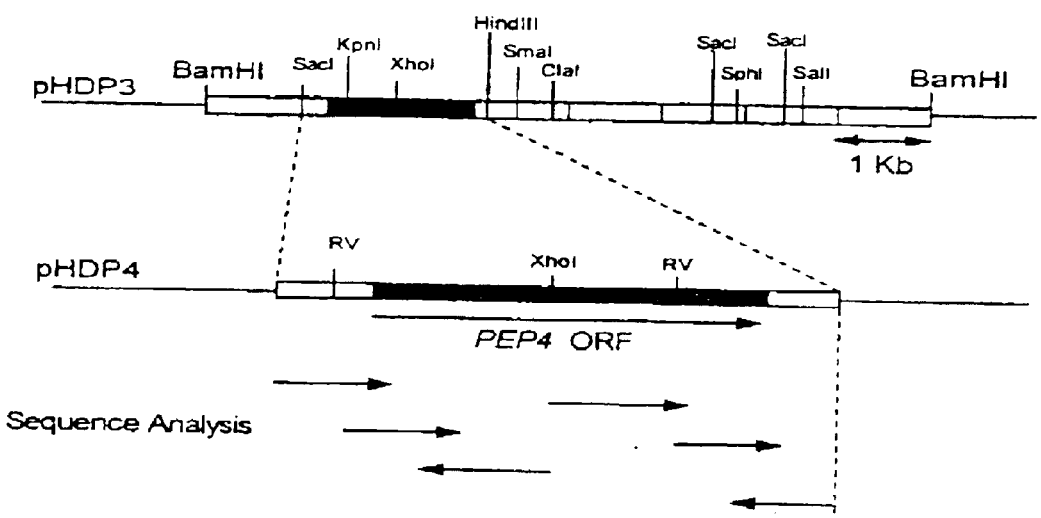
FIG. 2 is a restriction map of a *Hansenula polymorpha* PEP4 gene.

In order to obtain a PEP4 gene from the genomic DNA of *Hansenula polymorpha*, Southern blotting was conducted with the probe prepared in the first step. First after six aliquots of the genomic DNA obtained in the second step were treated with restriction enzymes BamHI, EcoRI, EcoRV, HindIII, PstI, and SalI, respectively, the resulting DNA fragments were fractionated on a 0.9% agarose gel by electrophoresis. The separated DNA molecules were transferred to a Nytran membrane (Schleicher & Schuell) by blotting, followed by exposing the membrane to the labeled probe under conditions favoring hybridization. The hybridization was conducted in the same manner as in the third step. A band that was dyed blue was observed in a DNA fragment which was cut into a length of about 8 kb by restriction enzyme BamHI. Next, the DNA fragment was isolated from the position at which the blue band appeared, and used to prepare a DNA library in the same manner as in the third step. The DNA library was subjected repetitively to Southern blotting to select a plasmid carrying the PRC1 gene, called plasmid pHDP3. Double digestion with restriction enzymes SacI/HindIII reduced the DNA fragment from about 8 kb to about 2.0 kb. The plasmid harboring the SacI/HindIII DNA fragment, was called pHDY4. It was deposited in the Korean Collection for Type Culture (KCTC), placed in Korea Research Institute of Bioscience and Biotechnology (KRIBB), #52, Oun-dong, Yusong-ku, Taejon 305–333, Republic of Korea, on the date of Feb. 18, 2000 and it was accepted under the accession number of KCTC 0733BP. The restriction site mapping and base sequencing of the *Hansenula polymorpha* DL1 PEP4 gene was conducted as illustrated in FIG. 2. The base sequence of the PEP4 gene is given in SEQ ID NO: 2. This DNA sequence was registered as U67173 with GenBank on Aug. 17, 1996. Analysis of the base sequence revealed that the *Hansenula polymorpha* DL1 PEP4 gene is 1,242 bp long with no introns and shows 52.4% homology to the base sequence of a *Sacchromyces cerevisiae* PRC1 gene. When being deduced from SEQ ID NO:2, the amino acid sequence of the *Hansenula polymorpha* DL1 PEP4 gene exhibits 50% homology to the protease A of *Sacchromyces cerevisiae*. In addition, high homology can be found in the $117^{th}$ amino acid reside, which is identified to be an aspartic acid acting as a catalytic group within an active site of aspartyl protease.

Fifth Step: Construction of Plasmid pKH3.9

In order to obtain a KEX1 gene from the genomic DNA of *Hansenula polymorpha*, Southern blotting was conducted with the probe prepared in the first step. First, after six aliquots of the genomic DNA obtained in the second step were treated with restriction enzymes BamHI, EcoRI, EcoRV, HindIII, PstI, and SalI, respectively, the resulting DNA fragments were subjected to electrophoresis on a 0.9% agarose gel. The separated DNA molecules were transferred to a Nytran membrane (Schleicher & Schuell) by blotting, followed by exposing the membrane to the labeled probe under conditions favoring hybridization. The hybridization was conducted in the same manner as in the third step, but using a modified hybrid solution (5×SSC, 0.1% N-lauryl sarcosine, 0.02% SDS, 2% blocking agent, 50% formamide). A band that was dyed blue was observed in a DNA fragment which was cut into a length of about 4.5 kb by restriction enzyme HindIII.

Figure 3:
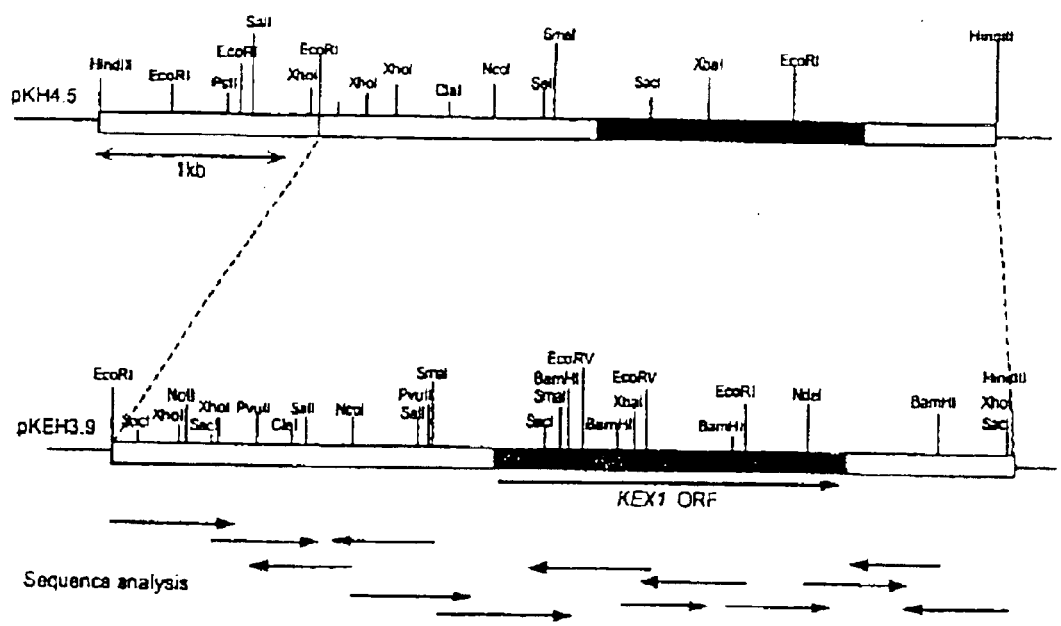
FIG. 3 is a restriction map of a *Hansenula polymorpha* KEX1 gene.

Next, the DNA fragment was isolated from the position at which the blue band appeared, and used to prepare a DNA library as in the third step. The DNA library was subjected repetitively to Southern blotting to select a plasmid carrying the PRC1 gene, called plasmid pKH4.5. The plasmid pKH4.5 was deposited in the Korean Collection for Type Culture (KCTC), placed in Korea Research Institute of Bioscience and Biotechnology(KRIBB), #52, Oun-dong, Yusong-ku, Taejon 305–333, Republic of Korea, on the date of Feb. 18, 2000 and it was accepted under the accession number of KCTC 0731BP. Double digestion with restriction enzymes EcoRI/HindIII reduced the DNA fragment from about 4.5 kb to about 3.9 kb. The plasmid harboring the EcoRI/HindIII DNA fragment, was called pKH3.9. The restriction site mapping and base sequencing of the *Hansenula polymorpha* DL1 PRC1 gene was conducted as illustrated in FIG. 3. The base sequence of the KEX1 gene is given in SEQ ID NO:3. This DNA sequence was registered as AF090325 with GenBank on Sep. 4, 1998. Analysis of the base sequence revealed that the *Hansenula polymorpha* DL1 KEX1 gene is 1,833 bp long with no introns. When being deduced from SEQ ID NO:3, the amino acid sequence of the *Hansenula polymorpha* DL1 KEX1 gene exhibits as low as 20% homology to the carboxypeptidase α of *Sacchromyces cerevisiae*. However, in the $176^{th}$ amino acid reside, which is identified to be a serine acting as a catalytic group within an active site of serine protease, there is found high homology to carboxypeptidase α as well as carboxypeptidase Y. Amino acid analysis according to Von Heijne's method (Von Heijne, *J. Mol. Biol.*, 173: 243 (1984)) divulged the presence of a signal peptide consisting of 18 amino acid residues.

Experiment 2: Preparation of Mutant Strains with Disrupted Plasmids

First Step: Construction of Disrupted Plasmid pHYL

Figure 4:
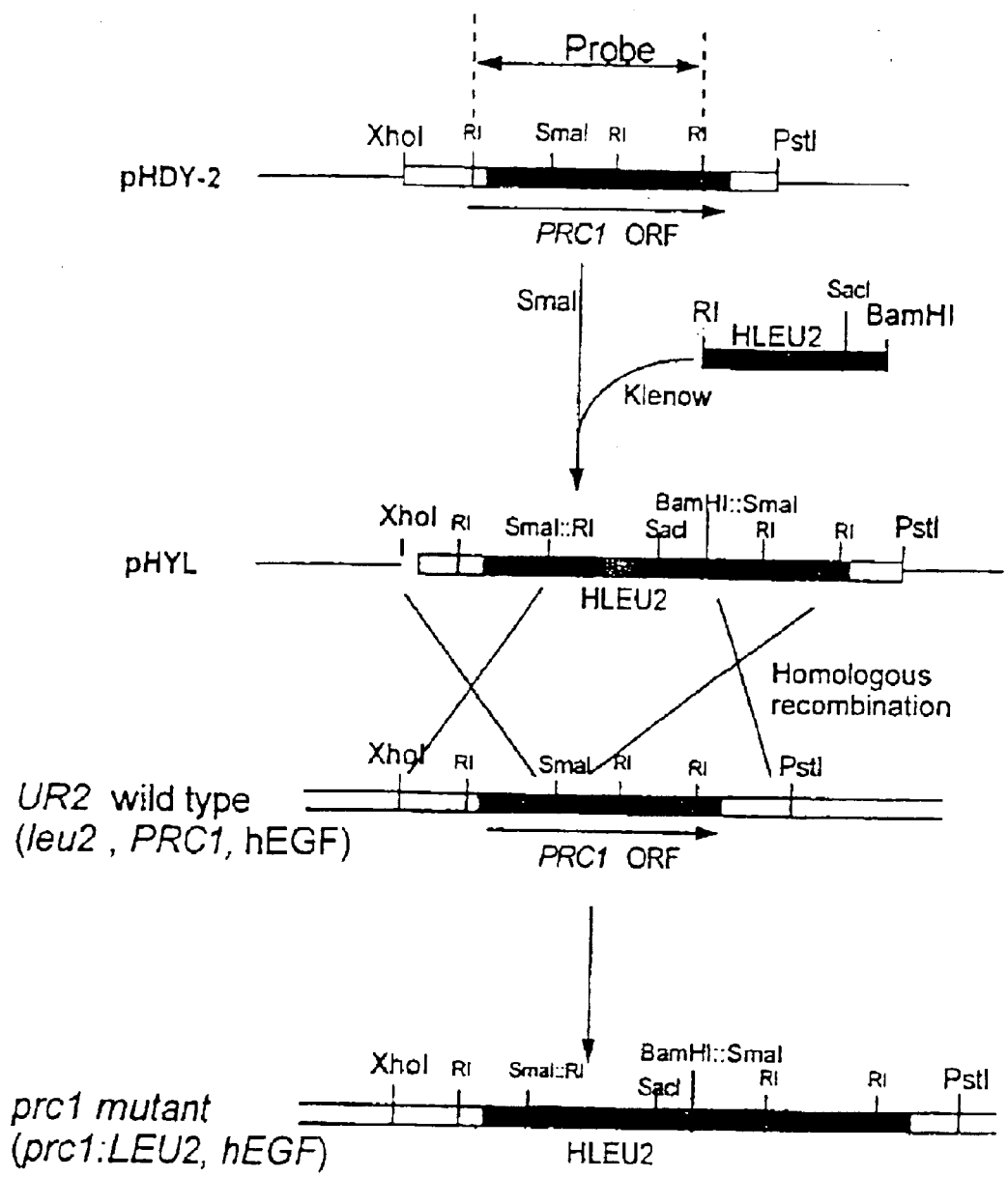
FIG. 4 shows the construction of a plasmid comprising a disrupted *Hansenula polymorpha* PRC1 gene by a LEU2 gene, which plasmid is useful to disrupt the PRC1 gene on the host genome, and its restriction map.

A LEU2 gene of *Hansenula polymorpha* was inserted into the PRC1 gene cloned in the plasmid pHDY2 constructed in the Experiment 1, as shown in FIG. 4. To this end, a 1.2 kb LEU2 gene fragment of *Hansenula polymorpha* was first obtained by the excision with restriction enzymes EcoRI and BamHI, and made blunt at its opposite ends through Klenow treatment. This blunt-ended LEU2 gene fragment was inserted to the SmaI site of the PRC1 gene on the plasmid pHDY2 to construct plasmid pHYL, which was used to disrupt the PRC1 gene coding for carboxypeptidase Y on the genome of *Hansenula polymorpha* DL-1, later.

Second Step: Construction of Disrupted Plasmid pHPL

Figure 6:
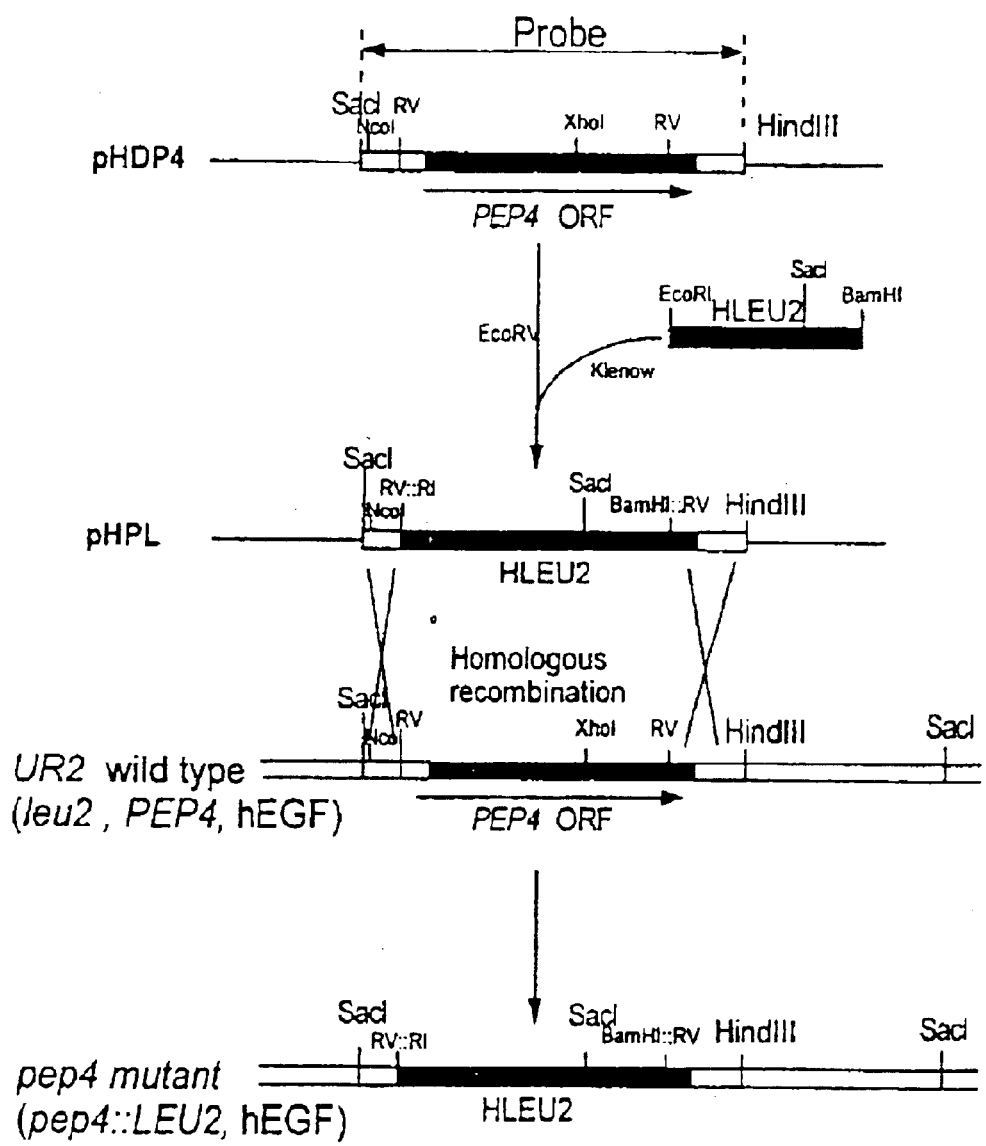
FIG. 6 shows the construction of a plasmid comprising a disrupted *Hansenula polymorpha* PEP4 gene by a LEU2 gene, which plasmid is useful to disrupt the PEP4 gene on the host genome, and its restriction map.

A LEU2 gene of *Hansenula polymorpha* was inserted into the PEP4 gene cloned in the plasmid pHDP4 constructed in the Experiment 1, as shown in FIG. 6. To this end, a 1.05 kb DNA fragment was removed from the PEP4 gene in the plasmid pHDP4 by use of restriction enzyme EcoRV while a 1.2 kb LEU2 gene fragment of *Hansenula polymorpha* obtained by the excision with restriction enzymes EcoRI and BamHI was made blunt at its opposite ends through Klenow treatment. Then, this blunt-ended LEU2 gene fragment was inserted into the truncated plasmid pHDP4, replacing the removed portion of the PEP4 gene, so as to give plasmid pHPL, which was used to disrupt the PEP4 gene coding for protease A on the genome of *Hansenula polymorpha* DL-1, later.

Third Step: Construction of Disrupted Plasmids pKUZ, pHYUZ, and pHPUZ

Figure 8:
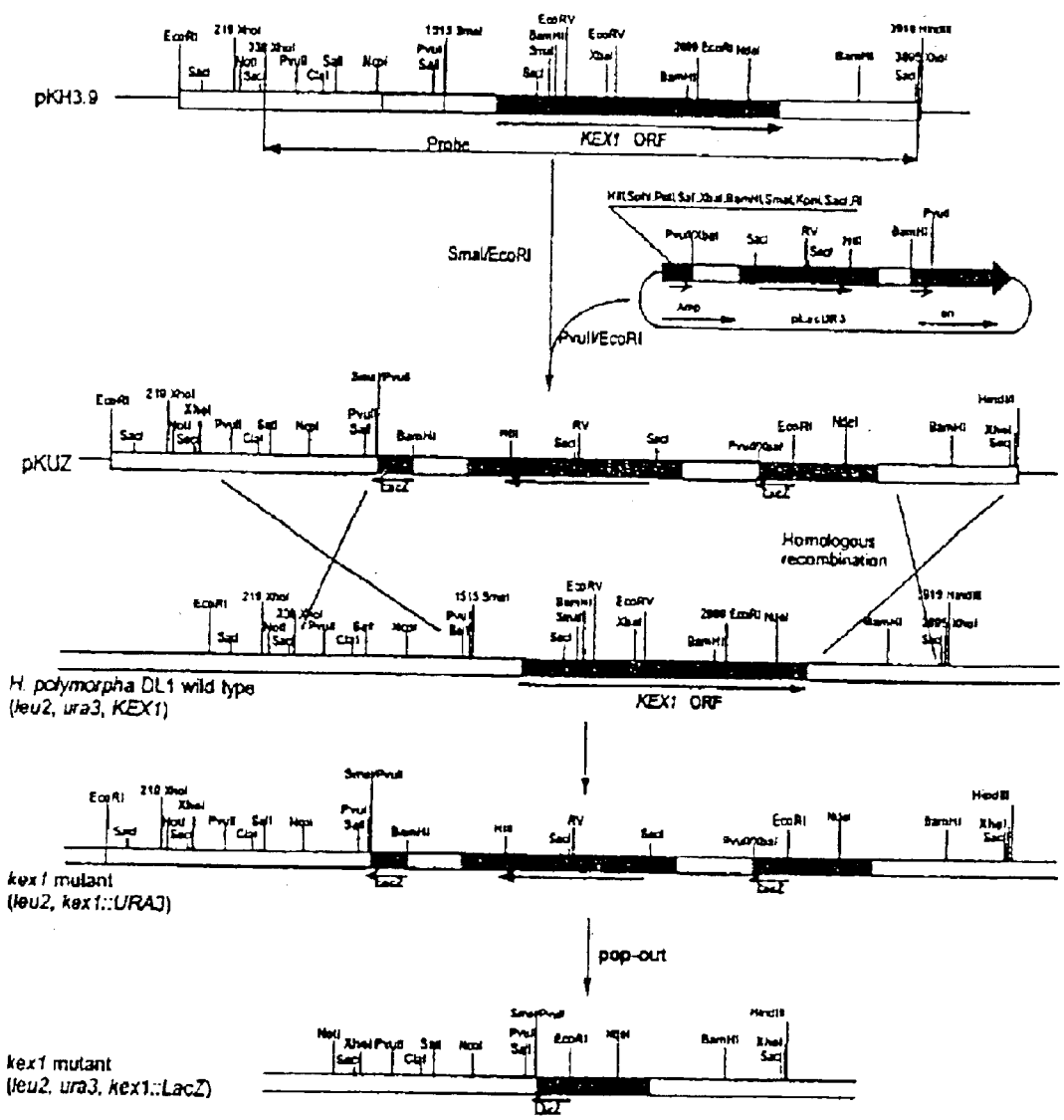
FIG. 8 shows the construction of a plasmid comprising a disrupted *Hansenula polymorpha* KEX1 gene by a URA3 gene, which plasmid is useful to disrupt the KEX1 gene on the host genome, and its restriction map.

In order to disrupt the cloned KEX1 gene of *Hansenula polymorpha* DL-1, there was constructed a pop-out cassette which was structured to allow a *Hansenula polymorpha* URA3 gene to be repetitively used as a selective marker, as shown in FIG. 8. In this regard, a BamHI/PvuII LacZ DNA fragment of 211 bp obtained from plasmid pUC19 was linked to each of the opposite ends of a *Hansenula polymorpha* URA3 gene of 1,323 bp in the same direction to prepare pop-out plasmid pLacUR3.

Separately, the plasmid pKH3.9 was digested with restriction enzyme SmaI and EcoRI to remove a 1,148 bp fragment comprising the promoter and a portion of the coding region. The pLacUR3 was cut with restriction enzymes PvuII and EcoRI to give a 1,735 bp *Hansenula polymorpha* URA3 gene fragment comprising two direct repeats of the 211 bp LacZ gene. This *Hansenula polymorpha* URA3 gene was linked to the truncated plasmid pKH3.9, replacing the 1,148 bp fragment, so as to construct plasmid pKUZ.

Figure 5:
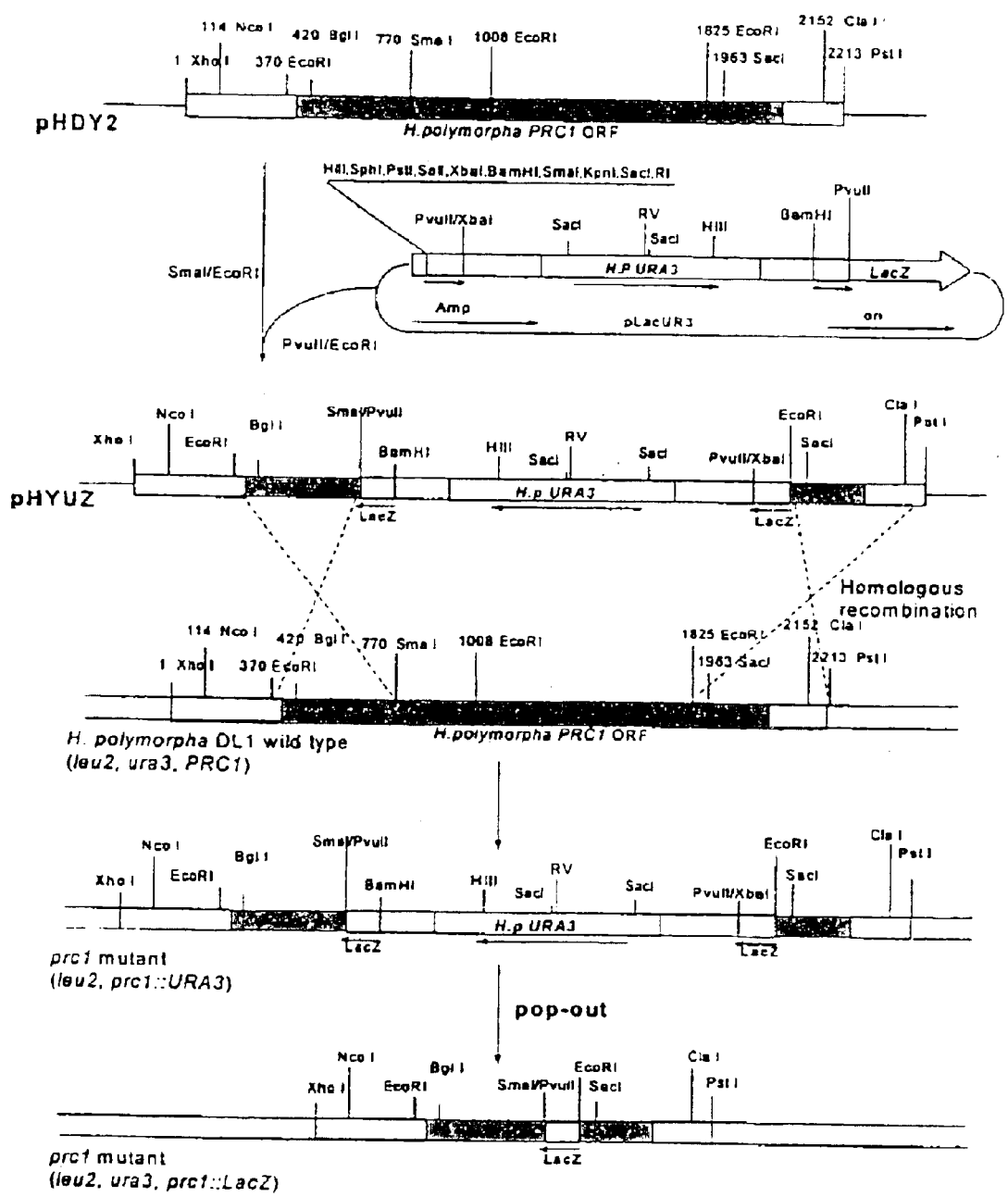
FIG. 5 shows the construction of a plasmid comprising a disrupted *Hansenula polymorpha* PRC1 gene by a URA3 gene, which plasmid is useful to disrupt the PRC1 gene on the host genome, and its restriction map.

As in the construction of the plasmid pKUZ, the pop-out plasmid pLacUR3 was treated with restriction enzymes PvuII and EcoRI to give a 1,735 bp *Hansenula polymorpha* URA3 gene fragment, which was then inserted into the plasmid pHDY2, replacing a 1,055 bp fragment comprising a portion of the coding region, which had been removed from the plasmid pHDY2 through the treatment with SmaI and EcoRI, as shown in FIG. 5. The resulting plasmid was called pHYUZ.

Figure 7:
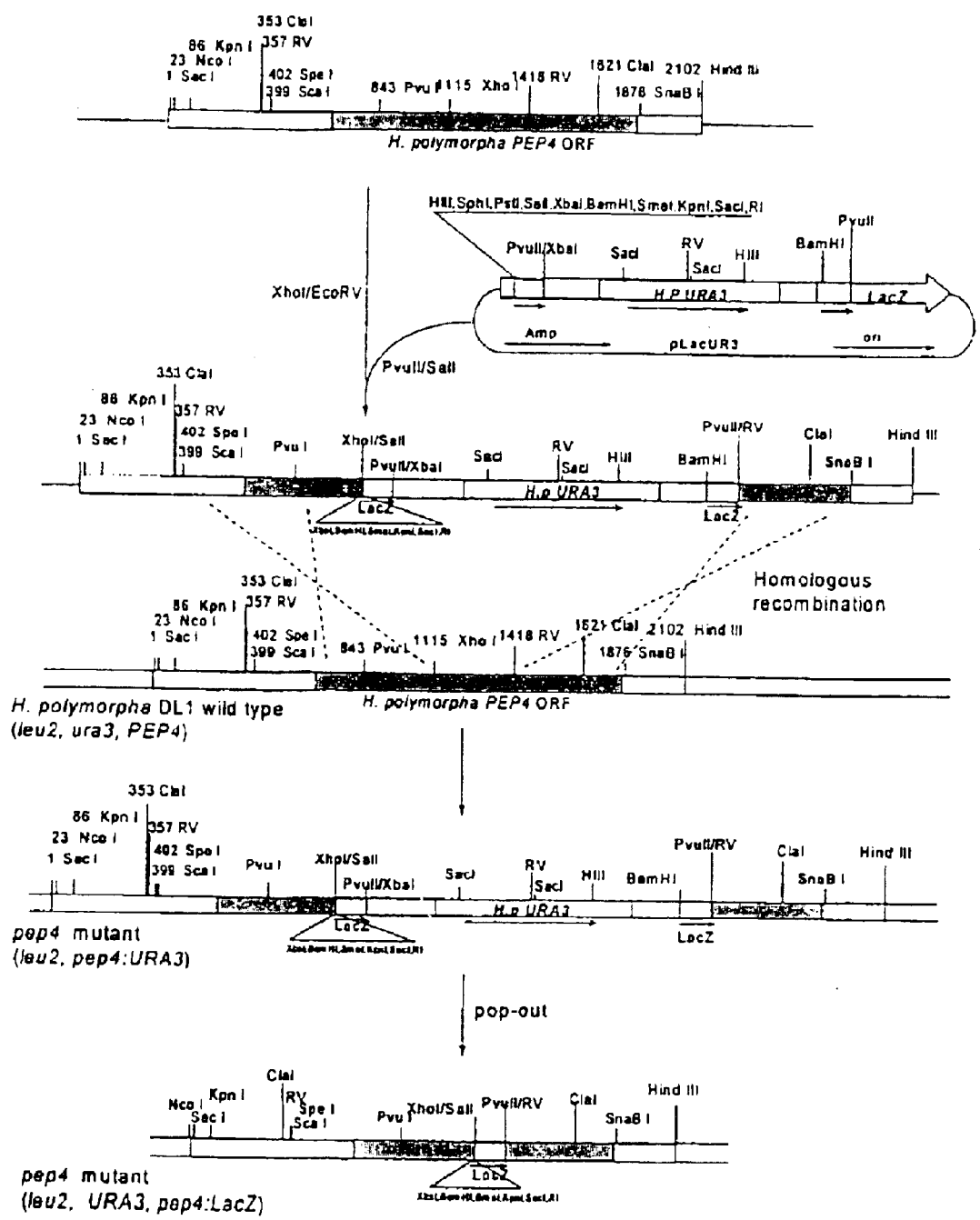
FIG. 7 shows the construction of a plasmid comprising a disrupted *Hansenula polymorpha* PEP4 gene by a URA3 gene, which plasmid is useful to disrupt the PEP4 gene on the host genome, and its restriction map.

Likewise, the cloned PEP4 gene of *Hansenula polymorpha* DL-1 in pHDP4 was disrupted by use of the pop-out cassette. A *Hansenula polymorpha* URA3 gene fragment 1,800 bp long, which was obtained by treating the pop-out plasmid pLacUR3 with restriction enzymes-PvuII and SalI, was inserted into the plasmid pHDP4, replacing a 303 bp fragment comprising a portion of the coding region, which had been excised from the plasmid pHDP4 by XhoI and EcoRV, as shown in FIG. 7. The resulting plasmid was called pHPUZ.

Fourth Step: Transformation with Disrupted Plasmid

Using the plasmid pKUZ constructed above, a *Hansenula polymorpha* DL1 strain (leu2, ura3, KEX1, PEP4, PRC1) was transformed into a carboxypeptidase α mutant strain (leu2, kex1::URA3, PEP4, PRC1) which was then cultured for more than 72 hours on a minimal solid medium (0.7% yeast base deficient in amino acids (YNB), 2% glucose, uracil 50 μg/mL, leucine 50 μg/mL, 2% agar) supplemented with 0.1% 5-fluoroorotic acid so as to select a URA3 gene pop-out strain of *Hansenula polymorpha* (leu2, ura3, kex1::LacZ, PEP4, PRC1). The *Hansenula polymorpha* DL1/Δkex1 was deposited in the Korean Collection for Type Culture(KCTC), places in Korea Research Institute of Bioscience and Biotechnology(KRIBB), #52, Oun-dong, Yusong-ku, Taejon 305–333, Republic of Korea, on the date of Feb. 18, 2000 and it was accepted under the accession number of KCTC 0736BP. This mutant strain was again transformed with the plasmid pHYUZ into a carboxypeptidase α/carboxypeptidase Y mutant strain (leu2, kex1::LacZ, prc1::URA3, PEP4). Culturing the carboxypeptidase α/carboxypeptidase Y mutant strain on a minimal solid medium supplemented with 0.1% 5-fluoroorotic acid afforded the selection of a URA3 gene pop-out strain (leu2, ura3, kex1::LacZ, prc1::LacZ, PEP4). Through the same transformation and culturing as in the above, the URA3 gene pop-out, carboxypeptidase α/carboxypeptidase Y mutant strain (leu2, ura3, kex1::LacZ, prc1::LacZ, PEP4) was converted into a URA3 gene pop-out, carboxypeptidase α/carboxypeptidase Y/protease A mutant strain (leu2, ura3, kex1::LacZ, prc1::LacZ, pep4::LacZ) with the aid of the plasmid pHPUZ.

Likewise, a combination of plasmids pHYUZ and pHPUZ was used to prepare a carboxypeptidase Y/protease A mutant strain (leu2, ura3, prc1::LacZ, pep4::LacZ, KEX1) while use of a combination of plasmids pKUZ and pHPUZ resulted in the preparation of a carboxypeptidase α/protease A mutant strain (leu2, ura3, kex1::LacZ, pep4::lacZ, PRC1).

Transformation of *Hansenula polymorpha* was conducted according to a lithium acetate method. A *Hansenula polymorpha* UR2 (leu2) strain which was highly productive of hEGF was cultured in a YEPD broth (peptone 2%, yeast extract 1%, glucose 2%) to the extent of OD6000=0.5. After being harvested, the cells were washed with an LiTE solution (0.1M Tris-Cl, pH 8.0, 10 mM EDTA, 10 mM LiAc, pH 7.5) and then, resuspended in 0.01 volume of LiTE solution to give competent cells. To 100 μl of the competent cells were added 0.5 g of a plasmid of interest, 10 μg of salmon sperm DNA, which was to serve as a carrier DNA, and 0.6 mL of a PEC/LiAc solution (40% PEG 4000, 0.1 M Tris-Cl, pH 8.0, 10 mM EDTA, 10 mM LiAc, pH 7.5). The resulting cell mixture was allowed to stand for 30 min at 30° C., added with 70 μl of DMSO, allowed to stand again at 42° C. for 15 min, and quenched in ice. After being harvested, the cells were cultured on a minimal solid medium (0.67% yeast base deficient in amino acids, 2% glucose, 2% azar) at 37° C. for 72 hours. For use in transformation, the plasmid pHYL was linearized by use of restriction enzymes HindIII/NcoI, the plasmid pKUZ by use of XhoI, the plasmid pHYUZ by use of XhoI/PstI, and the plasmid pHPUZ by use of SpeI/SnaBI.

Experiment 3: Measurement of Carboxypeptidase Y Mutant Strain and Protease A Mutant Strain for Carboxyeptidase Y Activity and Analysis of hEGF Produced from the Strains First Step: Measurement of Carboxypeptidase Y Mutant Strain and Protease A Mutant Strain for Carboxypeptidase Y Activity A 2.5 mg/mL solution of N-benzoly-L-tyrosine-p-nitroanilide in dimethylformamide and 0.1 M Tris-HCl (pH 7.5) were mixed in the volume ratio of 1:4 and 0.2 mL of the resulting solution was alloted to each well of a 96 well microtiter plate. The transformants obtained in Experiment 2 were inoculated into the wells and incubated at 37° C. for 16 hours. Based on the fact that a cell culture became yellow by the enzymatic action of active carboxypeptidase while a cell culture without active carboxypeptidase or with inactive carboxypeptidase remained colorless, absorbance at 450 nm was measured to select strains whose PRC1 gene was effectively disrupted. In addition, because the processing of carboxypeptidase Y was inhibited in protease A mutant strains, measurement of the activity of carboxypeptidase Y was utilized to select PEP4 gene-disrupted strains.

The results are given in Table 1, below. As shown in Table 1, nearly no activity of carboxypeptidase was detected in the carboxypeptidase Y mutant strain while the activity of carboxypeptidase Y was reduced by more than 60% in the protease A mutant strain. By these results, the genes PRC1 and PEP4 cloned in the invention were identified as coding for the carboxypeptidase Y and the protease A of *Hansenula polymorpha*, respectively. In addition, it was demonstrated that remarkable reduction was brought about in the activity of carboxypeptidase in the mutant strains which were disrupted in PRC1 and/or PEP4 gene. The transformed *Hansenula polymorpha* DL1/Δcpy and *Hansenula polymorpha* DL1/pep4 were deposited in the Korean Collection for Type Culture(KCTC), placed in Korea Research Institute of Bioscience and Biotechnology(KRIBB), #52, Oun-dong, Yusong-ku, Taejon 305–333, Republic of Korea, on the date of Feb. 18, 2000 and it were accepted under the accession number or KCTC 0735BP and KCTC 0734BP, respectively.

TABLE 1

Activity of Carboxypeptidase in Carboxypeptidase Y Mutant Strain

| Strains | Genotype | Carboxypeptidase A Activity (Abs) |
|---|---|---|
| *Hansenula polymorpha* UR2 | leu2, PEP4, PRC1, hEGF | 2.97 |
| REP4 Mutant | pep4::LEU2, PRC1, hEGF | 1.00 |
| PRC1 Mutant | prc1::LEU2, PEP4, hEGF | 0.10 |

Second Step: Confirmation of the Disruption By Southern Blotting

Southern blotting was conducted to confirm the disruption of the *Hansenula polymorpha* genes PRC1 and PEP4 with the *Hansenula polymorpha* gene LEU2 and the disruption of the *Hansenula polymorpha* gene KEX1 with the *Hansenula polymorpha* gene URA3. Each of the transformants selected in the fourth step of Experiment 3 was inoculated in a YEPD medium and cultured at 37° C. for 18–20 hours with shaking. After being harvested by centrifugation, the cells were suspended in 30 μl of an STES solution (0.5M NaCl, 0.01M EDTA, 1% SDD in 0.2M Tris-Cl, pH 7.6) in 1.5 mL tubes, added with 0.8 volumes of glass beads which were 0.4 mm in diameter, and voltexed for 5 min. Then, each tube was added with 200 μl of a TE buffer (1 mM EDTA in 10 mM Tris-Cl, pH 8.0) and 200 μl of phenol/chloroform/isoamylalchol (25:24:1) and voltexed for 2 min before being centrifuged at 12,000 rpm. To the supernatant was added 2.5 volumes of ethanol so as to precipitate the genomic DNA. 2–3 μg of the genome DNA was dissolved in deionized water.

This DNA solution was treated with restriction enzyme. Restriction enzyme EcoRI was used for the genomic DNA of the PRC1 gene-disrupted strain, restriction enzyme EcoRV for the genomic DNA of the PEP1 gene-disrupted strain, and restriction enzyme XhoI for the genomic DNA of the KEX1 gene-disrupted strain. The DNA molecules cut with the restriction enzymes were fractionated on 0.8% agarose gel by electrophoresis. The genes $PRC_1$, PEP4, and KEX1 shown respectively in FIGS. 1, 2 and 3 were used as probes for Southern blotting and the results are given in FIG. 9.

As seen in the blotted bands of FIG. 9, when the genomic DNA of the carboxypeptidase Y mutant strain was treated with restriction enzyme EcoRI, a LEU2 gene was inserted into a PRC1 fragment 0.65 kb long, to give a fused DNA fragment 1.85 kb long. Where the genomic DNA of the protease mutant strain was treated with restriction enzyme EcoRV, a single band corresponding to a size of 10 kb was detected because the EcoRV recognition site was removed in the course of replacing the LEU2 gene for a 1.1 kb EcoRV fragment of the PEP4 gene. Where the genomic DNA of the carboxypeptidase α mutant was cut with restriction enzyme XhoI, the URA3 gene was inserted into a 3.5 kb fragment of the KEX1 gene to give a fused DNA fragment 4 kb long. On the other hand, this extended DNA fragment was reduced to 2.5 kb as the URA3 gene was removed in the pop-out strain. Therefore, these results demonstrate that gene disruption was generated on the PRC1 and PEP4 genes by the LEU7 gene of *Hansenula polymorpha* and on the KEX gene by the URA3 gene of *Hansenula polymorpha*.

Third Step: Analysis of hEGF Secreted From Mutant Strains

For the analysis of the hEGF secreted from the mutants to YP-methanol media (yeast extract 1%, peptone 2%, methanol 2%), the cultures were subjected to centrifugation. The supernatants were allowed to undergo partial purification by use of Sep-Pak cartridge (C18, Waters, Millipore) and analyzed by HPLC. In connection with the partial purification, the Sep-Pak car-ridge was activated by the treatment with 10 ml of each of water, methanol, 0.1% trifluoroacetic acid, and 20% acetonitrile/0.1% trifluoroacetic acid and the culture supernatants controlled with 20% acetonitrile and 0.1% trifluoroacetic acid were allowed to pass through the activated Sep-Pak cartridge to absorb the proteins into the cartrige, followed by washing the cartridge with 20% acetonitrile and 0.1% triiluoroacetic acid to take off impurities. The hEGF absorbed was eluted three times with 1 mL of 50% acetonitrile and 0.1% trifluoroacetic acid. The eluates containing hEGF were concentrated by freeze-drying.

The samples partially purified were analyzed through reverse phase HPLC (Beckman Model 126 System) using 4.6×250 mm, 5 $\mu$m-C4 column (Vydac) for separating the samples. The mobile phase was moved at a flow rate of 0.3 mL/min while the concentration was increased from 20% acetonitrile, 0.1% trifluoroacetic acid to 60% acetonitrile, 0.1% trifluoroacetic acid for 35 min. Optical density at 215 mm was measured for the knowledge of sample separation. To determine whether the samples separated from HPLC contained HEG3 or not, the fractions at each peak were subjected to ELISA. For this, first, the samples each were suitably diluted in an antigen-coating buffer (0.1 M sodium carbonate buffer, pH 9.6) and the dilutions were added at an amount of 100 $\mu$l in each well of a microtiter plate well (Nunc-immunomodule) and reacted at 37° C. for 2 hours. The wells were washed with PBST (phosphate buffered saline+0.1% Tween 20), after which 100 $\mu$l of PBS containing 0.05% gelatin was added in each of the wells and allowed to stand at 37° C. for 30 min. After being washed with PBST, the wells each were added with 100 $\mu$l of an antibody solution which was obtained by diluting a monoclonal antibody against hEGF (UBI #05-109) 10,000 folds in a PBS containing 0.05% gelatin. Antigen-antibody reaction was conducted at 37° C. for 2 hours in the wells which were, then, washed with PBST. Horse radish-conjugated goat anti-mouse IgG (Bio-Rad) was diluted 3,000 folds in a PBS solution containing 0.05% gelatin, added at an amount of 100 $\mu$l per well and reacted at 37° C. for 1 hour. The wells were washed again with PBST before a coloring reaction. For coloration, a TMB substrate kit (Pierce) was used as a peroxidase substrate. This substrate was mixed at a ratio of 1:1 with a 0.02% solution of peroxide in a mixture of 0.04% TMB (3,3', 5,5'-tetramethyl benzidine) and citric acid buffer and added at an amount of 100 $\mu$l per well. After 15 min, 100 $\mu$l of 2M sulfuric acid stopped the enzyme-substrate reaction in each well. After completion of the color reaction, color quantitative analysis was achieved by measuring the absorbance at 450 nm in a 96-well plate autoreader (THERMO max, Molecular Devices, USA). As a control, recombinant hGF (UBI #01-107) was used in the amount range from 0.25 to 5 ng/well. As a result of the quantitative analysis, the expressed hEGF was detected in two fractions.

These fractions were freeze-dried for qualitative analysis. These two types of hEGF were analyzed for N-terminal amino acid sequence and molecular weight in the Korea Basic Science Institute. From two peaks, hEGF activity was detected. Of them, the relatively hydrophilic peak was found to have a molecular weight of 6,205 as measured by MALDI-Mass analysis. Therefore, it was a complete hEGF consisting of 53 amino acid residues. On the other hand, the hEGF of the relatively hydrophobic peak, eluted at a higher acetonitrile concentration, was measured to be 6,053 in molecular weight with 52 amino acid residues. Amino acid sequencing analysis read a sequence of Asn-Ser-Asp-Ser-Glu- (SEQ ID NO:10) in the N-terminal region of both the two types of hEGF, revealing that both hEGF molecules are separated accurately from the signal peptide by KEX2. Therefore, the hEGF consisting of 52 amino acid residues resulted from the separation of one amino acid reside from the C-terminal of the whole hEGF. That is, since the whole hEGF has a sequence of -Trp-Trp-Glu-Leu-Arg (SEQ ID NO:10) in its C-terminal region, the separation of the arginine residue from the full-length hEGF makes the resulting hEGF of 52 amino acid residues more hydrophobic.

With the information about the HPLC peaks obtained from the above analysis, the hEGF secreted from the *Hansenula polymorpha* UR strain was compared with that secreted from the protease-deficient mutant strain. The total amount of hEGF was lower in the protease A mutant strain than in the UR2 strain, but no great change could be found in the C-terminal decomposition therebetween. On the other hand, a significant carboxypeptidase Y disruption effect was brought about in the carboxypeptidase Y mutant strain. The hEGF which was not degraded in the C-terminal region hEGF, but intact, that is, the hEGF consisting of 53 amino acid residues amounted to 37% of the hEGF secreted from the UR2 strain, but increased to 57% in the carboxypeptidase Y mutant strain.

EXAMPLE II

Preparation of Methanol Oxidase (MOX) Gene-Disrupted *Hansenula polymorpha* Mutant Strain Experiment 1: Construction of pMLT-delta Vector for Disrupting MOX-TRP3 Gene The conversion of various yeasts, including *Sacchromyces cerevisiae*, into mutant strains in which particular genes are disrupted, is generally accomplished by selecting the transformants in which introduced selective marker cassettes are inserted into the genomes through the homologous double crossover at the sites of genes of interest (Rothstein, Meth. Enzymol. 101:202 (1983))). On the other hand, the introduced selective marker cassettes are inserted, for most part, into non-specific sites of the genome of *Hansenula polymorpha* through nonhomologous recombination. Accordingly, only a very low efficiency is imposed on the success in the preparation of a $\Delta$mox mutant *Hansenula polymorpha* strain in which a selective marker cassette is inserted into the genome through homologous double crossover at a site of the MOX gene to disrupt the MOX gene.

Figure 10:
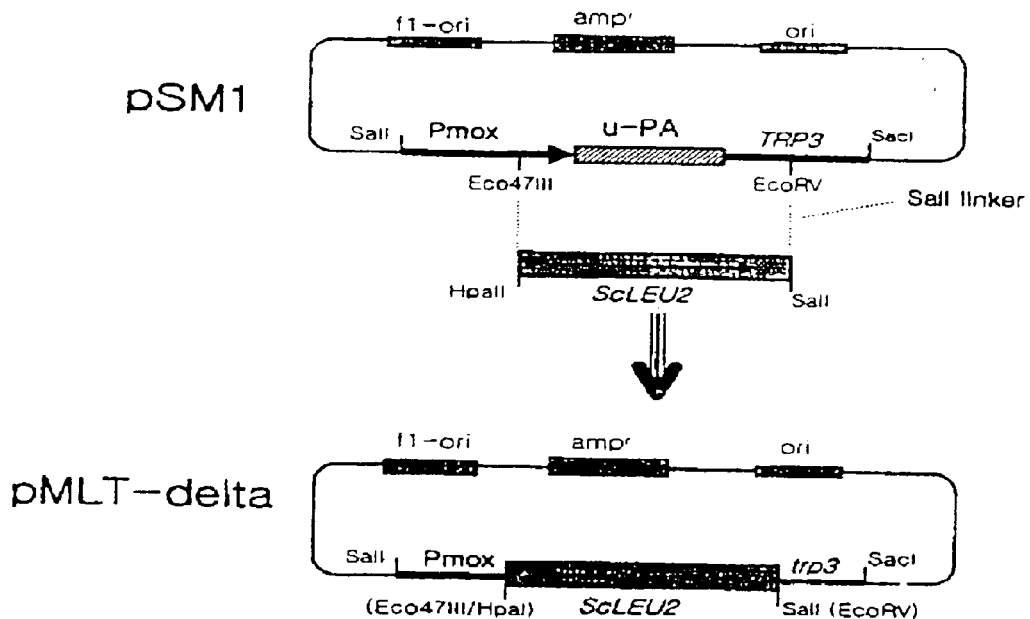
FIG. 10 shows the construction of vector pMLT-delta for disrupting MOX-TRP3 genes and its restriction map.

In order to facilitate a $\Delta$mox mutant *Hansenula polymorpha* strain whose MOX gene is disrupted, the MOX gene and the TRP3 gene, which is immediately adjacent to the MOX gene, were both disrupted on the basis of the previous research result of the present inventors (Agaphonov et al., Yeast 11:1241 (1995)), which discloses that the TRP gene (Reid G. A., Nucl. Acids Res. 16, 6236) can be disrupted to the extent of 2% by homologous recombination and an expression cassette carrying a MOX promoter and a DNA segment of the TRP3 gene can be inserted into the genome through the homologous recombination at MOX promoter and TRP3 gene sites to select TRP$^-$ transformants. To this end, first, a well known vector pSM1 (Agaphonov et al., Yeast 11:1241 (1995)) was digested with Eco47III/EcoRV to delete a 2.5 kb DNA fragment comprising a portion of a MOX promoter, a whole urokinase gene, and a portion of a TRP3 gene. Separately, a well known vector YEp13 (Broach et al., Gene 8, 121 (1979)) was digested with HpaI/SalI to excise a 2 kb DNA fragment which carried a LEU2 gene derived from Saccharomyces. Replacing the deleted 2.5 kb DNA fragment, the obtained 2 kb DNA fragment was ligated to the linearized pSM1 vector to construct vector pMLT-delta which is capable of disrupting, a MOX gene and a TRP gene at once. This construction scheme is illustrated in FIG. 10. As shown in FIG. 10, pMLT-delta has as a selective maker for *Hansenula polymorpha* a *S. cerevisiae* LEU2 gene which is flanked with a portion of a MOX promoter and a portion of a TRP3 gene (mox(p)::*S. cerevisiae* LEU2::trp3).

*E. coli* DH5α harboring the vector pMLT-delta useful to disrupt MOX-TP3 genes was deposited in the Korean Collection for Type Culture of Korea Research Institute of Bioscience and Biotechnology under the Accession No. KCTC 0727BP on Feb. 10, 2000.

Experiment 2: Construction of Novel Δmox Mutant DLT2 and Characterization

As a mother strain for the preparation of a MOX-TRP3 gene-disrupted mutant, there was employed DL1-L (leu2), a leu-auxotrophic *Hansenula polymorpha* DL-1 (ATCC 26012)-derived mutant.

Figure 11:
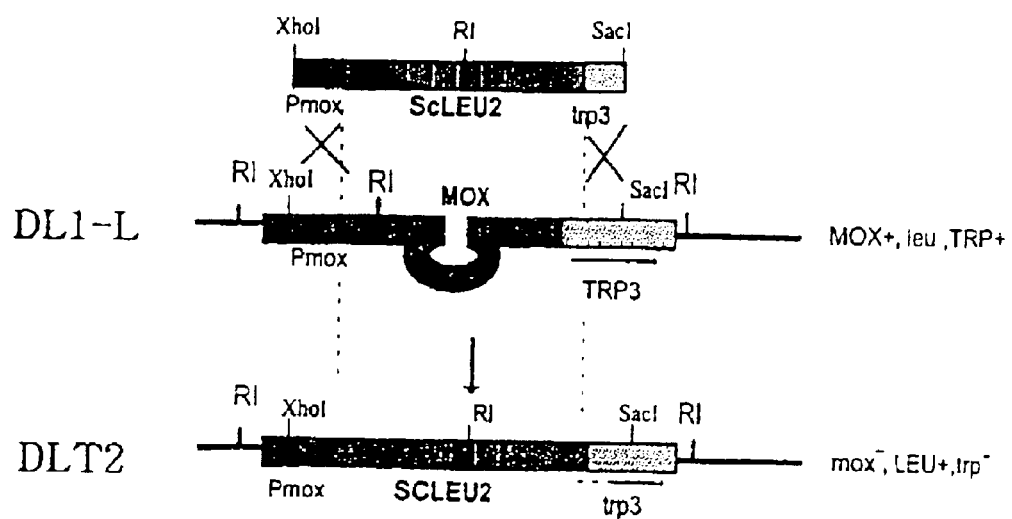
FIG. 11 shows the change on the genome upon the preparation of Δmox mutant DLT2 with the vector pMLT-delta.

The vector pMLT-delta obtained above was cut with restriction enzymes XhoI and SacI and introduced, according to the Hill method (Hill et al., *Nucl. Acids Res.* 19: 5791(1991)) into *Hansenula polymorpha* DL1-L(leu2) which was, then, cultured on a tryptophane-containing minimal solid medium (2% glucose, 0.67% amino acid-deficient yeast base, 20 mg/L tryptophane) to primarily select LEU$^+$ transformants. With the aim of selecting a trp$^-$, mox$^-$ transformants (FIG. 11) in which the introduced mox(p)::*S. cerevisiae* LEU2::trp3 cassette was inserted into the MOX promoter and TRP3 gene site through homologous recombination, an observation was made whether these LEU$^-$ transformants could be grown on a tryptophane-deficient medium containing methanol as a sole carbon source. Through the Southern blotting using a MOX promoter and a TRP3 gene fragment as probes, the selected trp$^-$, mox$^-$ transformants were investigated as to whether a major part of the MOX gene and a portion of the TRP3 gene on their genome were distrupted. The finally selected mutant was called DLT2 (leu2 mox trp::LEU2). Because DLT2 cannot produce methanol oxidase any more owing to the disruption of the MOX gene on the genome, its consumption rate of methanol is greatly reduced compared with MOX wild type DL1-L's, making it virtually impossible for DLT2 to grow in the medium containing methanol as a sole carbon source, as apparent from the results of FIGS. 12A and 12B. In addition, the mutant cannot be grown in tryptophane-deficient media or YPD medium (2% glucose, 2% peptone, 1% yeast extract) on account of TRP3 gene distruption, as seen in FIGS. 12C, 12D and 12E.

This Δmox mutant DLT2 was deposited in the Korean Collection for Type Culture of Korea Research Institute of Bioscience and Biotechnology under the accession No. KCTC 0728BP on Feb. 10, 2000.

Experiment 3: Insertion of Expression Vector Into MOX Gene Region of DLT2 and Pop-Out Therefrom

Figure 13A:
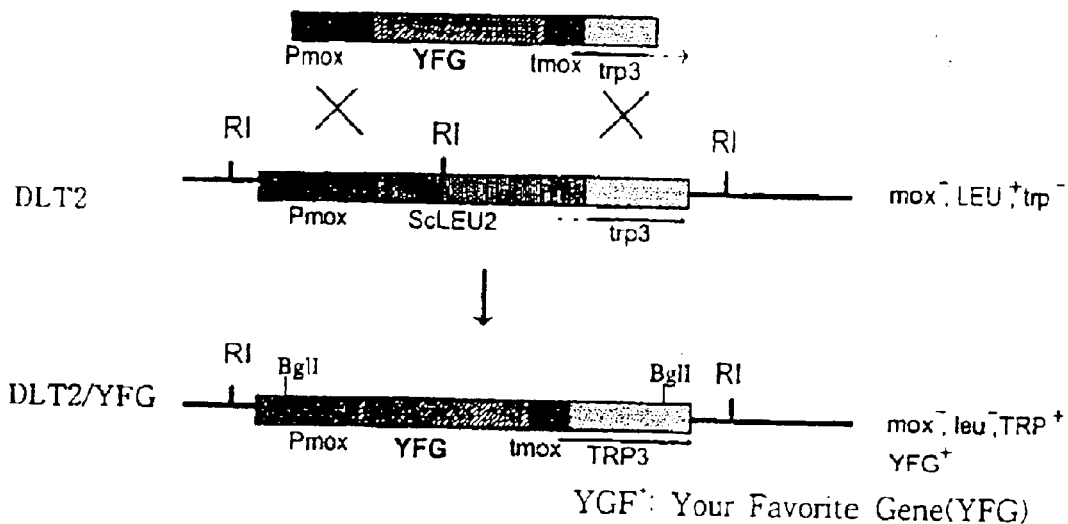
FIG. 13 shows the feasibility of the transformation from wild type to a mutant and vice versa: introduction of an recombinant protein expression cassette into a MOX gene site of the Δmox mutant DLT2 (A); Popping out of the expression cassette from the transformed DLT2 (B); and Returning to MOX wild type (C)

*Hansenula polymorpha* is transformed mainly through nonhomologous recombination, so that most of the introduced expression vectors are inserted into non-specific sites on the genome. However, in the event that an expression cassette which comprised a MOX promoter and a portion of a TRP3 gene at its opposite ends respectively was introduced into the DLT2 host, which is of Δmox as well as Δtrp, there could be obtained TRP$^-$ transformants as a result of the homologous recombination at the MOX promoter and TRP3 gene site on the genome. That is, the transformants in which the expression cassette was inserted into the MOX gene site (FIG. 13A) could be selected with relative ease.

Figure 13B:
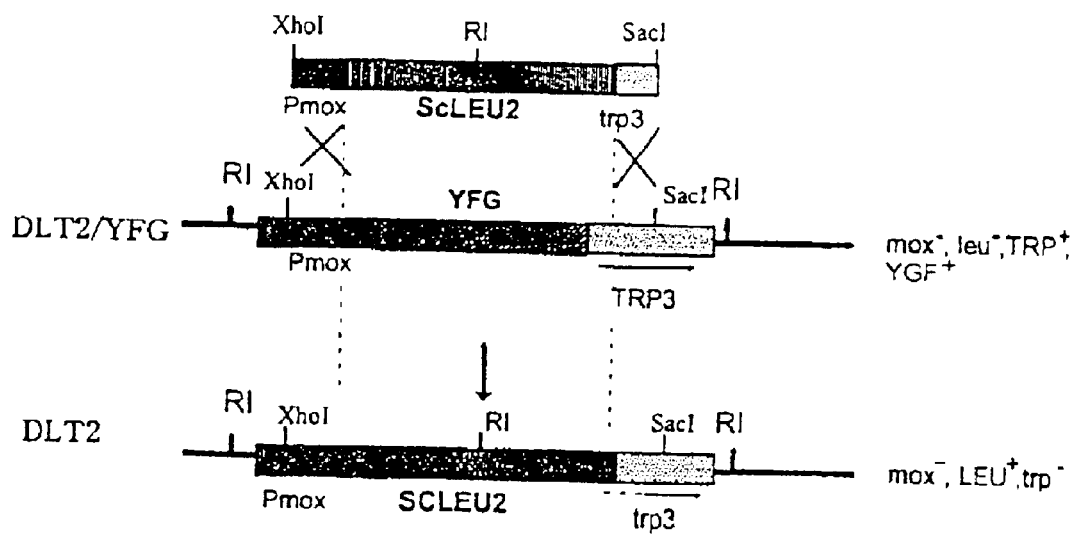

Furthermore, where the inserted expression vector would be popped out later, the vector pMLT-delta cut with XhoI and SacI, which had been used for the preparation of DLT2 in the above experiment 2, was introduced again into the recombinant DLT2 strain to select LEU$^-$ transformants. Identification as to whether the transformants were of mox$^-$, trp$^-$ phenotype and expressed preexisting recombinant proteins assured the removal of the preexisting recombinant expression vector from the genome through the homologous recombination, as illustrated in FIG. 13B. By this technique, a DLT2 transformant harboring an old expression vector could be returned to its original DLT2, which was thus ready to adopt a new expression vector comprising a MOX promoter and a portion of a TRP3 gene at its MOX site.

Figure 13C:
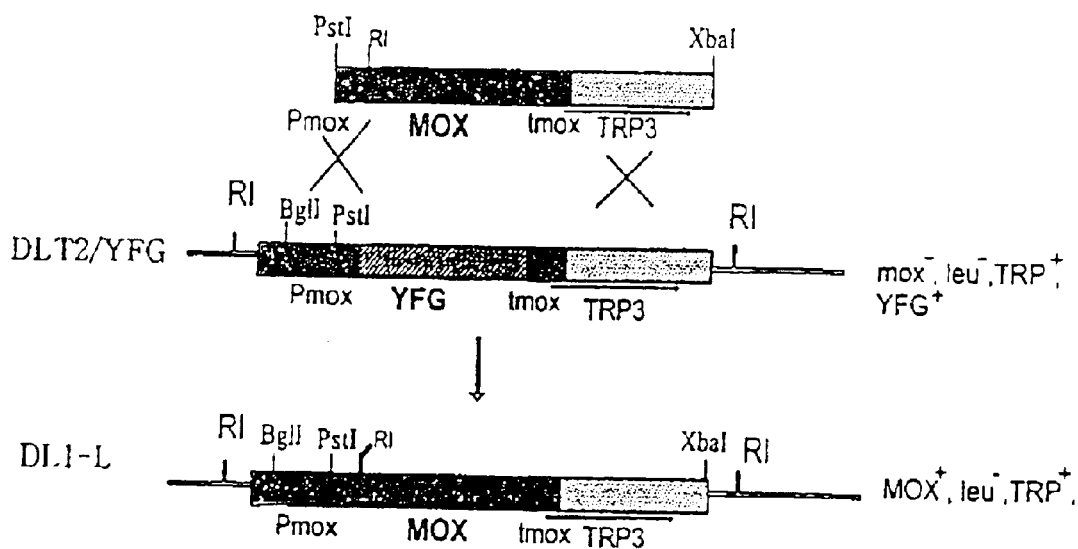

In addition, a 3.5 kb DNA fragment comprising a MOX gene and a TRP3 gene was obtained by cutting pMOX36616 (KRIBB report BSKG 1050-885-3) with restriction enzymes PstI/XbaI and introduced into DLT2 transformants. Of them, the transformant that rapidly grew on a synthetic medium supplemented with methanol and leucine was selected. That is, the preexisting expression vector inserted into the MOX gene was popped out to revive the MOX gene, which led to the conversion of the DLT2 transformant into a MOX$^-$ strain, as illustrated in FIG. 13C.

Consequently, after DLT2 transformants are mutated, the previously inserted expression vectors can be removed and replaced with new expression vectors on the host genomes. Alternatively, mutants of desired phenotypes can be prepared under the background of MOX$^-$ wild type. Therefore, the pop-out technique for expression vectors inserted into host genomes allows previously developed mutant strains to be used as hosts for producing various recombinant proteins.

Experiment 4: Comparison of Recombinant Protein Expression Efficiency Between MOX Wild Type and Δmox Mutant To compare the recombinant protein expression efficiency of a MOX wild type with that of a Δmox mutant strain, DL1-L was used as the MOX wild type while the DLT2, prepared in the above experiment 2, was selected for the mutant strain. The recombinant protein of interest was human urinary plasminogen kinase (u-PA), simply called urokinase. Into the MOX gene site of the DLT2 strain (leu2 mox-trp3::ScLEU2), vector pSM1 (Agaphonov et al., Yeast 11: 1241 (1995)) carrying a u-PA expression cassette in which a u-PA gene is linked to a MOX promoter, was introduced to obtain a Δmox transformant which could express u-PA. On the other hand, a MOX transformant capable of expressing u-PA was prepared by introducing vector pKSM8 (Agaphonov et al., unpublished result), which carries the same u-PA expression cassette, but uses HLEU2-d (Agaphonov et al., Yeast 15: 541 (1999)) as a selective marker, into DL1-L(leu2) and selecting a LEU$^-$ transformant.

After being cultured in YPD medium (yeast extract 1%, bacto-peptone 2%, dextrose 2%) for 18 hours, the transformants selected were inoculated into IM medium (yeast extract 1%, bacto-peptone 3%, methanol 2%) at an amount of 17% and cultured for 70 hours with shaking. The u-PA secreted into cell cultures was analyzed for activity with the aid of fibrin plates in accordance with the Astrup method (Astrup et al., Arch. *Biochem. Biophys.* 40: 346 (1952)). Because the Δmox transformant grows at a lower rate in IM medium containing methanol as a main carbon source than does the MOX transformant, the u-PA activity of cell cultures obtained after 70 hours of the cultivation was calibrated against the total amount of cell proteins and expressed as IU per mg of total cell protein (IU/mg of t.c.p.). The results are given in Table 2, below. As apparent from the data of Table 2, the u-PA expression efficiency of the Δmox transformant is four times as much as that of the MOX transformant, demonstrating that the DLT2 strain is excellent as a u-PA producing host.

TABLE 2

Expression Efficiency of Urokinase in *Hansenula polymorpha* MOX Wild Type (DL1-L) and Δmox Mutant (DLT2) After Shake Culturing in Flask

| # | MOX status | U-PA activity (IU/ml) | Specific Activity (IU/mg of t.c.p.) | Mean Value (IU/mg of t.c.p.) |
|---|---|---|---|---|
| 1 | MOX | 19 | 6.8 | 7.6 |
| 2 | | 25 | 9.2 | |
| 3 | | 22 | 6.9 | |
| 4 | Δmox | 28 | 28 | 29.6 |
| 5 | | 18 | 23 | |
| 6 | | 29 | 36 | |
| 7 | | 25 | 34 | |
| 8 | | 26 | 27 | |

Experiment 5: Production of Recombinant Albumin in Δmox Mutant DLT2

Using human serum albumin(HSA), comparison was also conducted for the recombinant expression efficiency between a MOX wild type and a Δmox transformant. For this, there was first constructed a recombinant albumin expression cassette in which a gene coding for human serum albumin was inserted between a MOX promoter and a TRP3 gene fragment. By introducing the albumin cassette into a MOX gene site of the Δmox mutant DLT2, a transformant DLT2/HSA was prepared (Kang et al., unpublished) and deposited in the Korean Collection for Type Culture of the Korea Research Institute of Bioscience and Biotechnology (KTBB) under the accession number KCTC 0740BP on Mar. 2, 2000. As a transformant in which the albumin expression cassette was introduced into a MOX gene site of the MOX wild type, there was employed DL1-1/T7 which had been prepared in previous research (Korean Pat. Appl'n No. 133190). These transformants were seed-cultured for 16–20 hours in YPG medium (yeast extract 1%, bacto-peptone 2%, glycerol 2%) and then, cultured for 72 hours with shaking in 250 ml baffled flasks containing expression-inducing YPM medium (yeast extract 1%, bacto-peptone 2%, methanol 2%). As for albumin quantification, the albumin secreted into the cell cultures was measured by Western blotting (Kang et al., J. Microbiol. Biotechnol. 8, 42 (1998)) while the intensity of appearing bands was read with the aid of a densitometer (Bio-Rad, Model GS-700).

Figure 14:
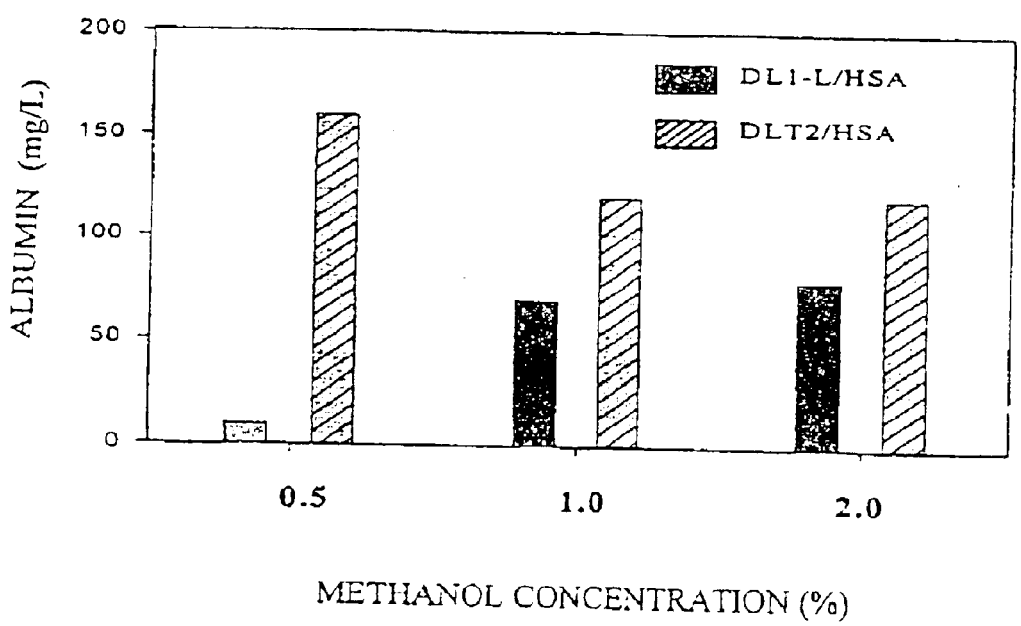
FIG. 14 is a histogram showing the expression of albumin in the MOX DL-1L and the Δmox mutant DLT2.

Because the Δmox mutant DLT2 hardly grows in YPM medium which use methanol as a sole carbon source as descried in the above experiments 2 and 4, the transformants were cultured in two steps for comparison. In detail, the transformants were first cultured in 50 ml of YPG medium supplemented with glycerol and then, the total cells harvested by centrifugation were inoculated at a high density into 25 ml of YPM medium. Under the culturing condition of such methanol medium, the inocula did not grow further, but the albumin production continued to be conducted by virtue of the presence of the MOX promoter. As for the Δmox transformant DL1-L/HSA, it produced albumin at an amount of about 120 mg/L when being cultured in 2% methanol-containing YPM medium in flask, as shown in FIG. 14. This was about twice greater than the albumin amount produced when the MOX transformant DL1-L/T7 was cultured at a high density, indicating the possibility that the Δmox strain might be more productive of recombinant proteins than might the MOX wild type even when being cultured at a high density in a large-scale fermentation bath for the mass production of recombinant proteins. Particularly, when the methanol concentration was lowered to 0.5%, the albumin production of DLT2/HSA was increased rather than decreased, whereas DL1-L/T7 was greatly degraded in albumin expression efficiency because the methanol was rapidly consumed as a carbon source. Therefore, the Δmox strain has another advance over the MOX wild type in that recombinant proteins can be obtained at high efficiency without continuously feeding methanol and the fermentation process is relatively simple.

Experiment 6: Use of the Pop-Out Technique to Development of Novel Mutant Strains as Hosts for General Use in Producing Various Recombinant Proteins The plasmid shuffling technique to facilitate the removal of the expression vector from the host cell has been well developed in the traditional yeast *S. cerevisiae*, where most expression cassettes were retained in an episomal vector capable of extrachromosomal replication (Boeke et al., Meth. Enzymol. 154, 164, 1987). The technique provides the *S. cerevisiae* expression system with a powerful means to allow mutant strains, derived from a parental recombinant strain, to be developed as useful host strains for general in producing various heterologous proteins. A recombinant *S. cerevisiae*, strain expressing a reporter protein, which can be easily analyzed, can be mutagenized and screened for the desired phenotype such as super-secretion. After removal of the pre-existent expression vector from the obtained mutants strain of *S. cerevisiae*, another expression vector can be introduced into the mutants strains to express other recombinant proteins. By contrast, this kind of procedure has been unable to be carried out in the *H. polymorpha* system mainly due to the non-specific integration of expression vector into the host chromosomal DNA.

Figure 15:
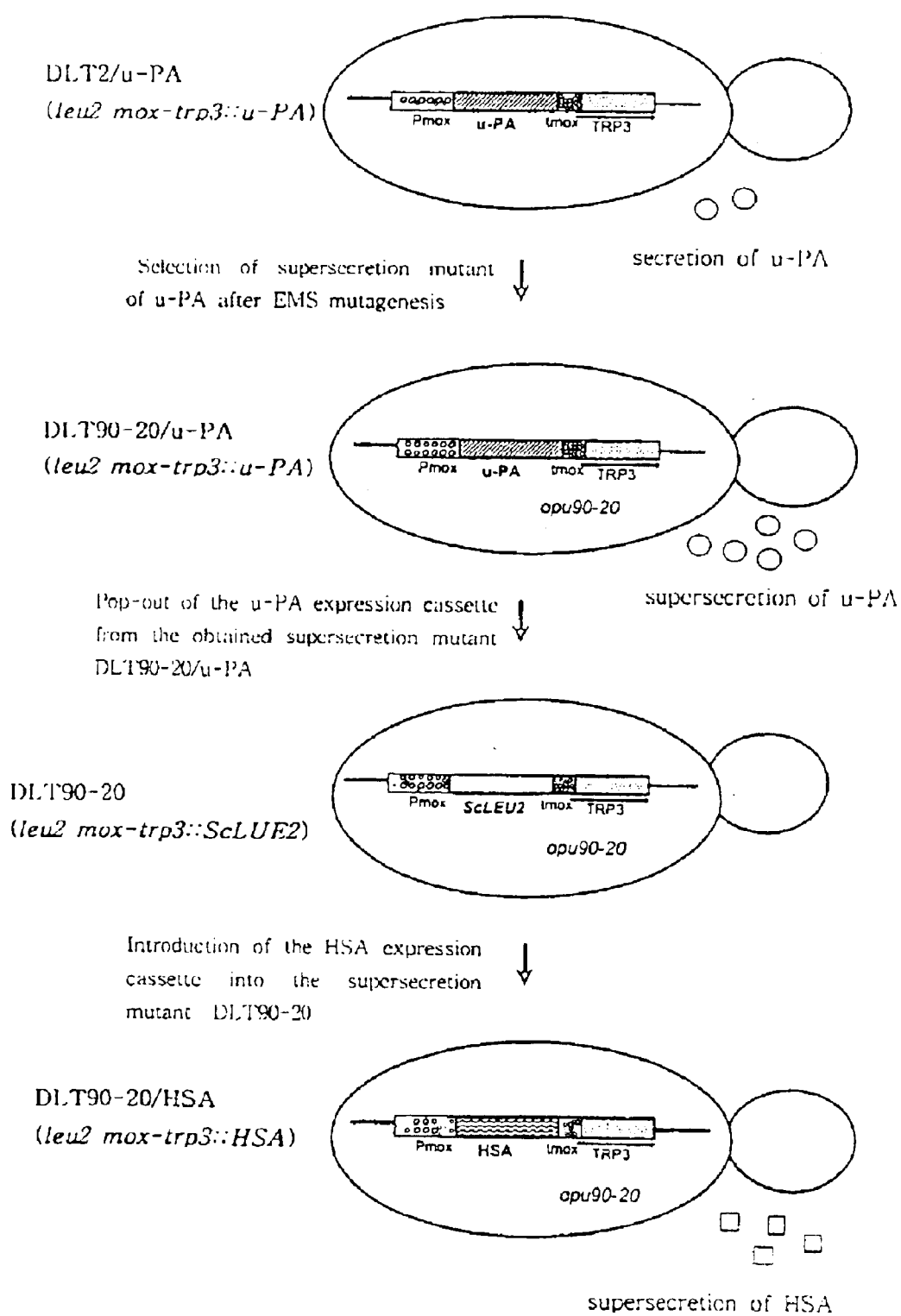
FIG. 15 shows the process to develop super-secretion mutant strains as the general host strains for the production of recombinant proteins using the pop-out technique.

However, the present invention of DLT2 provides the *H. polymorpha* system with the pop-out technique in which a recombinant protein expression cassette integrated into the host chromosome can be efficiently popped out therefrom, as shown in the above experiment 3. The activity of U-PA can be also easily analyzed by the plate assay. Therefore, using the recombinant DLT2/u-PA (leu2 mox-trp3::u-PA) expressing u-PA as the parental strain, which was constructed in the above experiment 4, we carried out the experiment to isolate super-secretion mutant strains therefrom and to develop the obtained mutant strains as the general host strains for the production of other recombinant proteins (FIG. 15). To obtain mutant strains with the increased secretion capacity, the recombinant DLT2/u-PA was undergone with the mutagenesis caused by the chemical mutagen, ethyl methane sulfonate (EMS). After incubation in 3.5% EMS solution for 33 min and subsequent neutralization with 6% thiosulfate nitrium, the mutagenized cells were plated into the fibrin plate (Agaphonov et al., Yeast 15, 541, 1999) and compared with the parental strain DLT2/u-PA for the secretion capacity of u-PA. Among several super-secretion mutants showing at least more than two-fold improved secretion, a mutant named DLT-90-20/u-PA (leu2 mox-trp3::u-PA opu90-20) with the three-fold improvement in the u-PA secretion was chosen to be developed as the general host strain for the production of other heterologous proteins. As described in the FIG. 13B of the above experiment 3, the XhoI/SacI truncated pMLT-delta was reintroduced into the DLT-90-20/u-PA mutant strain for the selection of LEU+ transformants. Subsequently, the mox-, trp- transformants were selected therefrom and the pop-out of the u-PA expression cassette was confirmed on the fibrin plate. In this procedure, the DLT90-20 mutant strain was converted to have the MOX-TRP3 genes disrupted with the ScLEU2 cassette like the original strain DLT2. To exploit the obtained super-secretion mutant DLT90-20 (leu2 mox-trp3::ScLEU2 opu90-20) as the host for the production of other recombinant proteins, the HSA expression cassette was inserted into the MOX gene site of DLT90-20 according to the procedure explained in the above experiment 5. The resultant recombinant strain DLT90-20/HSA was compared with the DLT2/HSA, which was constructed in the above experiment 5, for the production capacity of HSA. The DLT90-20/HSA strain showed 150% improvement in the HSA secretion than the DLT2.HSA, indicating that the super-secretion mutant 90-20 is also useful for the production of HSA. The present result demonstrates that another major advantage of the DLT2 strain in the present invention over the previous host strains of H. polymorpha is the feasibility of pop-out technique, which allows the obtained novel mutant strains to be utilized as a general host strain for the production of various recombinant proteins in the H. polymorpha expression system.

INDUSTRIAL APPLICABILITY

As described hereinbefore, the present invention can bring about a great improvement in the expression efficiency of the recombinant pretein producing system through Hansenula polymorpha as well as in the simplification of the fermentation procedure. In addition, the present invention provides a technique by which Hansenula polymorpha is allowed to be used as a general host for producing various proteins.

The Hansenula polymorpha carboxypeptidase Y mutant strain in which the gene PRC1 coding for carboxypeptidase Y is disrupted, is found to be lower in the carboxyl terminal degradation of an exogenous protein, e.g., hEGF by as much as 40% than the wild type. The Hansenula polymorpha strain in which the gene KEX1 coding for carboxypeptidase α is disrupted in addition to the gene PRC1 coding for carboxypeptidase Y, is further decreased in the carboxyl terminal degradation of exogenous proteins. As for the Hansenula polymorpha protease A mutant strain in which the gene PEP4 coding for protease A is disrupted, it does not exhibit a decrease in the carboxy terminal degradation of hEGF, but is greatly decreased in degrading other exogenous proteins at their carboxyl terminals. In addition, the Hansenula polymorpha Δmox mutant, which is transformed with the vector pMLT-delta useful to disrupt MOX and TRP3 genes, can play an excellent role as a host in producing various proteins without continuous feeding of methanol because the expression cassette enables the expression of recombinant proteins to be induced at high efficiency in a medium containing a low concentration of methanol. Furthermore, the expression cassette inserted into a MOX gene site of the genome of the Δmox mutant strain can be popped out effectively. Thence, after mutation is caused in a Δmox transformant, a new expression vector can be re-introduced replacing the previously inserted expression vector, or mutants of desired phenotypes can be prepared under the background of MOX⁻ wild type. Therefore, the mutants previously developed can fulfill themselves as hosts for general use in producing various proteins.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. An isolated nucleic acid comprising SEQ ID NO:3.

* * * * *